(12) United States Patent
Contreras-Vidal et al.

(10) Patent No.: US 11,413,210 B2
(45) Date of Patent: Aug. 16, 2022

(54) CUSTOMIZABLE ORTHOTIC/PROSTHETIC BRACES AND LIGHTWEIGHT MODULAR EXOSKELETON

(71) Applicant: University of Houston System, Houston, TX (US)

(72) Inventors: Jose Luis Contreras-Vidal, Houston, TX (US); Jeffrey Joseph Gorges, Houston, TX (US); Atilla Kilicarslan, Houston, TX (US)

(73) Assignee: University of Houston System, Houston, TX (US)

( * ) Notice: Subject to any disclaimer, the term of this patent is extended or adjusted under 35 U.S.C. 154(b) by 468 days.

(21) Appl. No.: 16/308,964

(22) PCT Filed: Jun. 14, 2017

(86) PCT No.: PCT/US2017/037457
§ 371 (c)(1),
(2) Date: Dec. 11, 2018

(87) PCT Pub. No.: WO2017/218661
PCT Pub. Date: Dec. 21, 2017

(65) Prior Publication Data
US 2019/0328604 A1    Oct. 31, 2019

Related U.S. Application Data

(60) Provisional application No. 62/349,921, filed on Jun. 14, 2016.

(51) Int. Cl.
*A61H 3/00* (2006.01)
*A61F 5/01* (2006.01)
(Continued)

(52) U.S. Cl.
CPC .............. *A61H 3/00* (2013.01); *A61F 5/0123* (2013.01); *A61H 1/0262* (2013.01); *A61H 3/02* (2013.01);
(Continued)

(58) Field of Classification Search
CPC . B25J 9/0006; A61H 3/00; A61H 3/02; A61H 2003/007; A61H 2201/165;
(Continued)

(56) References Cited

U.S. PATENT DOCUMENTS 5,522,402 A    6/1996   Cooley
6,821,233 B1   11/2004  Colombo et al.
(Continued)

FOREIGN PATENT DOCUMENTS

EP    2671544 A2    12/2013
EP    2708211 A1    3/2014
(Continued)

OTHER PUBLICATIONS

Kids don't walk like scaled-down adults. Journal of Experimental Biology (2021) 224, jeb243739. doi:10.1242/jeb.243739 2021.
(Continued)

*Primary Examiner* — Valerie L Woodward
*Assistant Examiner* — Paige Kathleen Bugg
(74) *Attorney, Agent, or Firm* — Shackelford, Bowen, McKinley & Norton, LLP

(57) ABSTRACT

Improved customizable orthotic/prosthetic braces and a lightweight modular exoskeleton may aid individuals with lower limb motor impairment, including children. These customizable orthotic/prosthetic braces improve the strength and rigidity of such braces without a weight penalty. A structural frame is embedded between an inner shell and outer shell, which comprise materials that are easily moldable to conform to a user's limb. The lightweight modular (Continued)

exoskeleton system provides six (6) joint actuators, which are designed to be modular, that act as the active joints (e.g. hips, knees, and ankles) of the exoskeleton. Additionally, the exoskeleton may also provide four (4) passive joints for inversion/eversion of the legs and feet. Foot, crutch, and hip assemblies may also be provided for the exoskeleton. Further, the six joint actuators may be utilized between the hip brace assembly and thigh brace assembly, the thigh and shank brace assembly, and the shank brace assembly and foot assembly, where the braces may correspond to the customizable orthotic/prosthetic design. The modularity of the actuators and braces allows for exoskeleton assemblies that can be tailored to patient specific needs.

19 Claims, 21 Drawing Sheets

(51) Int. Cl.
  *A61H 1/02* (2006.01)
  *A61H 3/02* (2006.01)
(52) U.S. Cl.
  CPC ............ *A61H 2003/007* (2013.01); *A61H 2201/1215* (2013.01); *A61H 2201/165* (2013.01); *A61H 2201/1642* (2013.01); *A61H 2201/5061* (2013.01); *A61H 2201/5066* (2013.01); *A61H 2201/5079* (2013.01); *A61H 2201/5082* (2013.01)
(58) Field of Classification Search
  CPC .... A61H 2201/1436; A61H 2201/1463; A61H 2201/1481; A61H 2201/1654; A61H 2201/1688; A61H 2201/1697; A61H 1/0255; A61H 1/0262; A61H 1/0237; A61H 1/024; A61H 1/0244; A61H 2201/0248; A61H 2201/0251; A61F 2/604; A61F 2/64; A61F 2/642; A61F 2/644; A61F 2/646; A61F 2/66; A61F 2/607; A61F 2002/648; A61F 5/0102; A61F 5/0123; A61F 5/0125; A61F 5/0127; A61F 5/013; A61F 5/0106; A61F 5/00; A61F 5/01; A61F 5/0104; A61F 5/05; A61F 5/0585; A61F 5/05858; A61F 2005/0132; A61F 7/02; A61F 13/00; A61F 13/04

USPC .......................................................... 601/5
See application file for complete search history.

(56) References Cited

U.S. PATENT DOCUMENTS

| | | | |
|---|---|---|---|
| 7,947,004 B2 | 5/2011 | Kazerooni et al. | |
| 2006/0052731 A1* | 3/2006 | Shimada | A61H 3/00 602/5 |
| 2009/0306801 A1 | 12/2009 | Sivak et al. | |
| 2010/0094188 A1* | 4/2010 | Goffer | A61H 1/0266 602/23 |
| 2010/0145239 A1* | 6/2010 | Kudoh | A61H 3/00 601/34 |
| 2011/0066088 A1 | 3/2011 | Little et al. | |
| 2011/0288611 A1* | 11/2011 | Lunau | A61N 1/0408 607/51 |
| 2013/0253385 A1 | 9/2013 | Goffer et al. | |
| 2014/0100493 A1 | 4/2014 | Craig et al. | |
| 2014/0196757 A1* | 7/2014 | Goffer | A61H 1/0262 135/66 |
| 2014/0365003 A1* | 12/2014 | Takahashi | B25J 9/0087 700/245 |
| 2015/0012111 A1 | 1/2015 | Contreras-Vidal et al. | |
| 2015/0051527 A1* | 2/2015 | Potter | A61F 5/0125 602/16 |
| 2015/0272810 A1* | 10/2015 | Teng | A61H 1/0244 601/34 |
| 2015/0337938 A1* | 11/2015 | Jones | F16H 49/001 74/409 |
| 2015/0351991 A1 | 12/2015 | Amundson et al. | |
| 2016/0128890 A1* | 5/2016 | LaChappelle | A61F 2/70 623/30 |
| 2016/0139666 A1 | 5/2016 | Rubin et al. | |
| 2017/0297278 A1* | 10/2017 | LeCursi | A61F 5/028 |
| 2017/0312153 A1* | 11/2017 | Paul | A61G 5/14 |
| 2019/0064018 A1* | 2/2019 | Miyazawa | B25J 19/02 |

FOREIGN PATENT DOCUMENTS

| | | | | |
|---|---|---|---|---|
| KR | 100716597 B1 | 5/2007 | | |
| WO | WO-2016146960 A1 * | 9/2016 | ............ | B25J 9/0006 |

OTHER PUBLICATIONS

Simple models highlight differences in the walking biomechanics of young children and adults. Journal of Experimental Biology (2021) 224, jeb243040. doi:10.1242/jeb.243040.

* cited by examiner

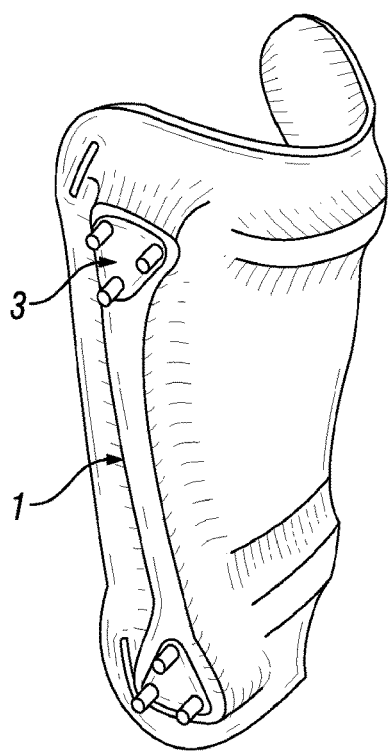
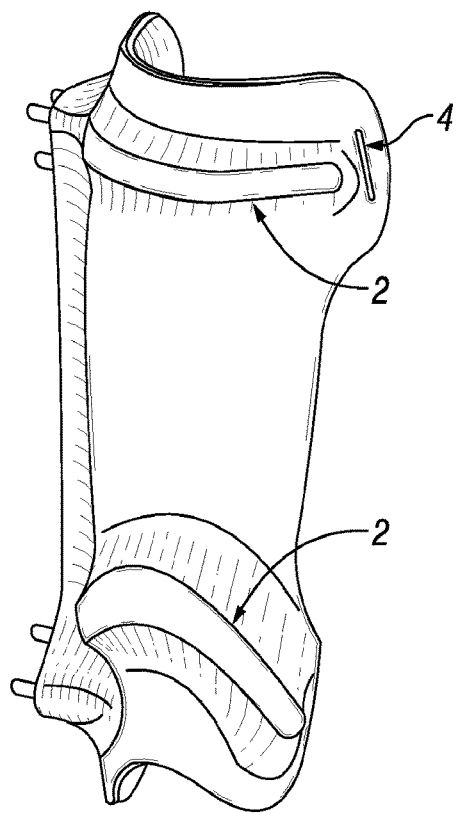
FIG. 5A  FIG. 5B
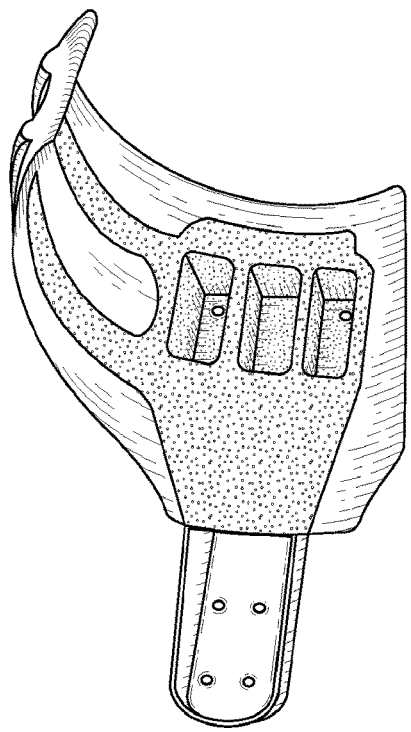
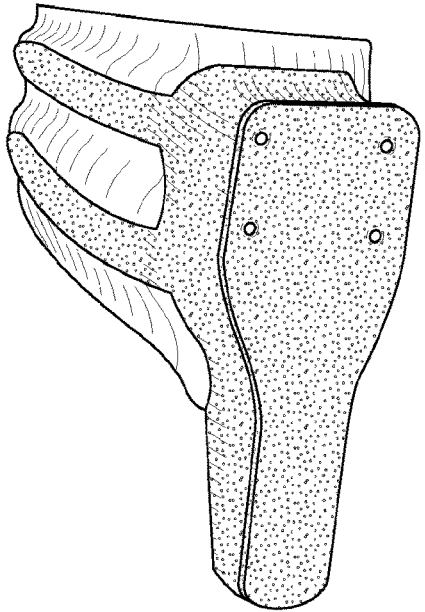
FIG. 5C  FIG. 5D

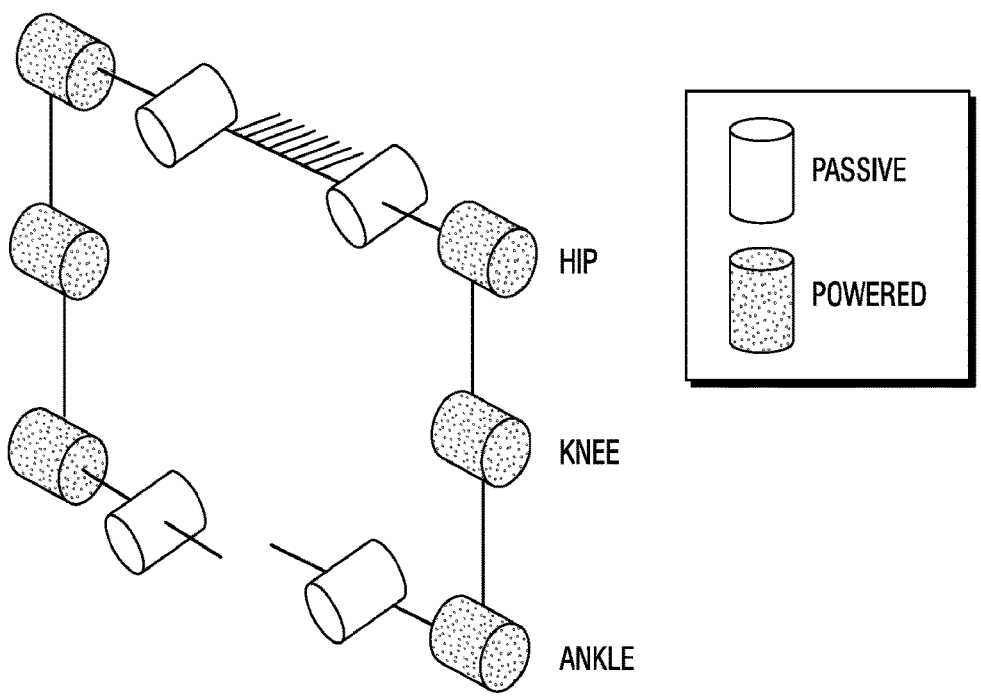
FIG. 10
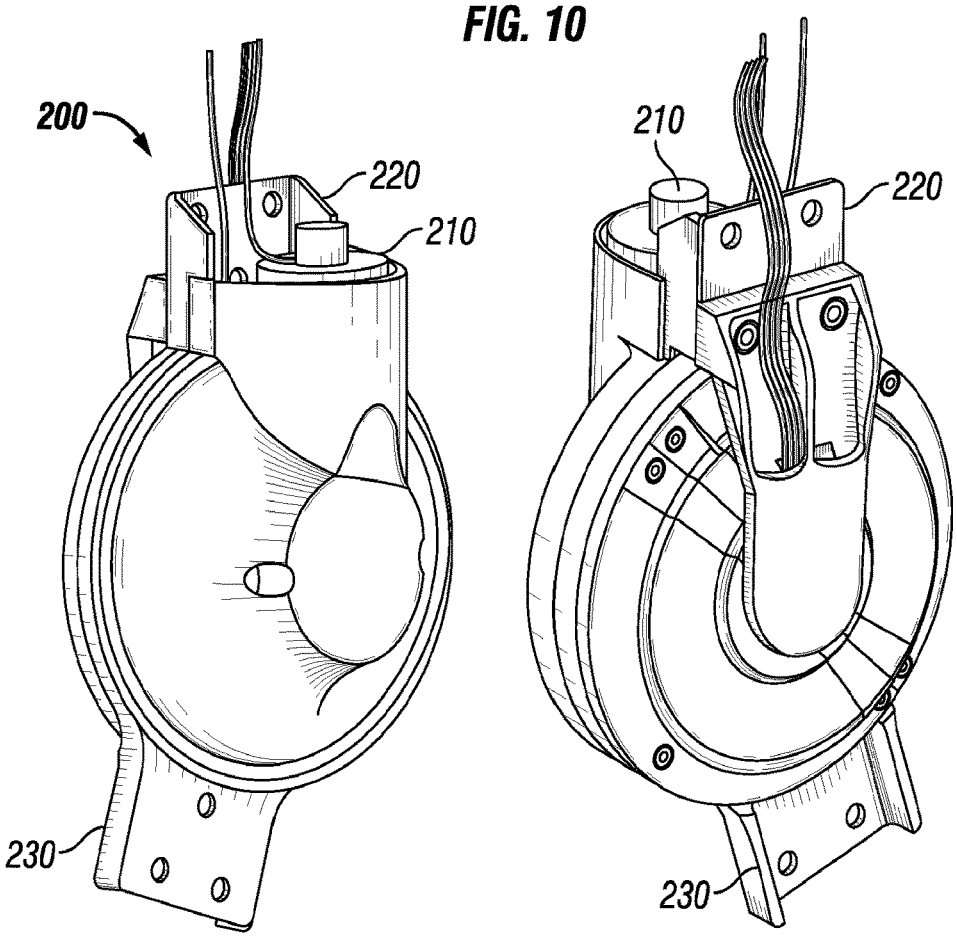
FIG. 11A    FIG. 11B

SECTION A-A
SCALE 1 : 2.5

DETAIL B
SCALE 2 : 2.5

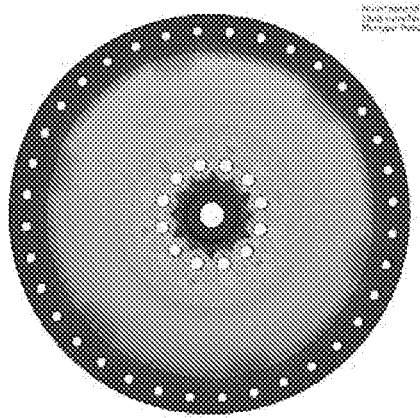 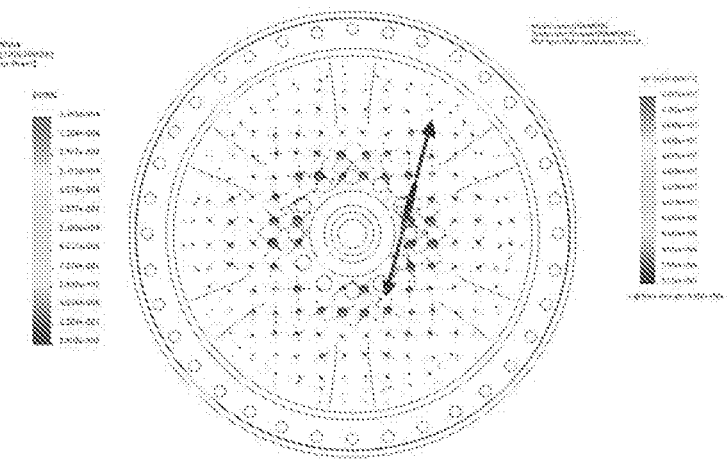
Figure 20A                    Figure 20B

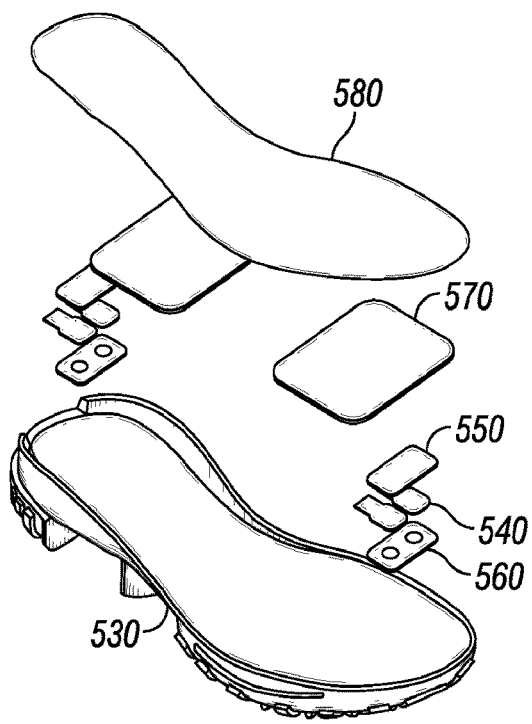
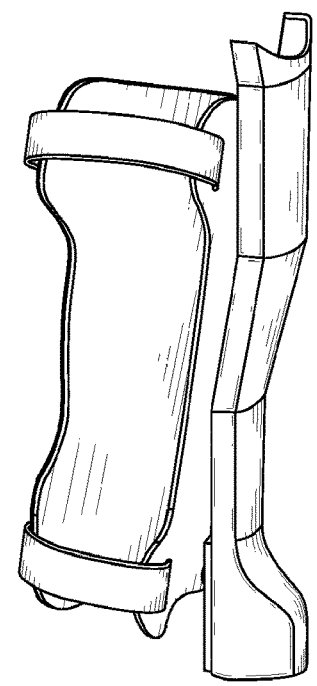
FIG. 28  FIG. 29
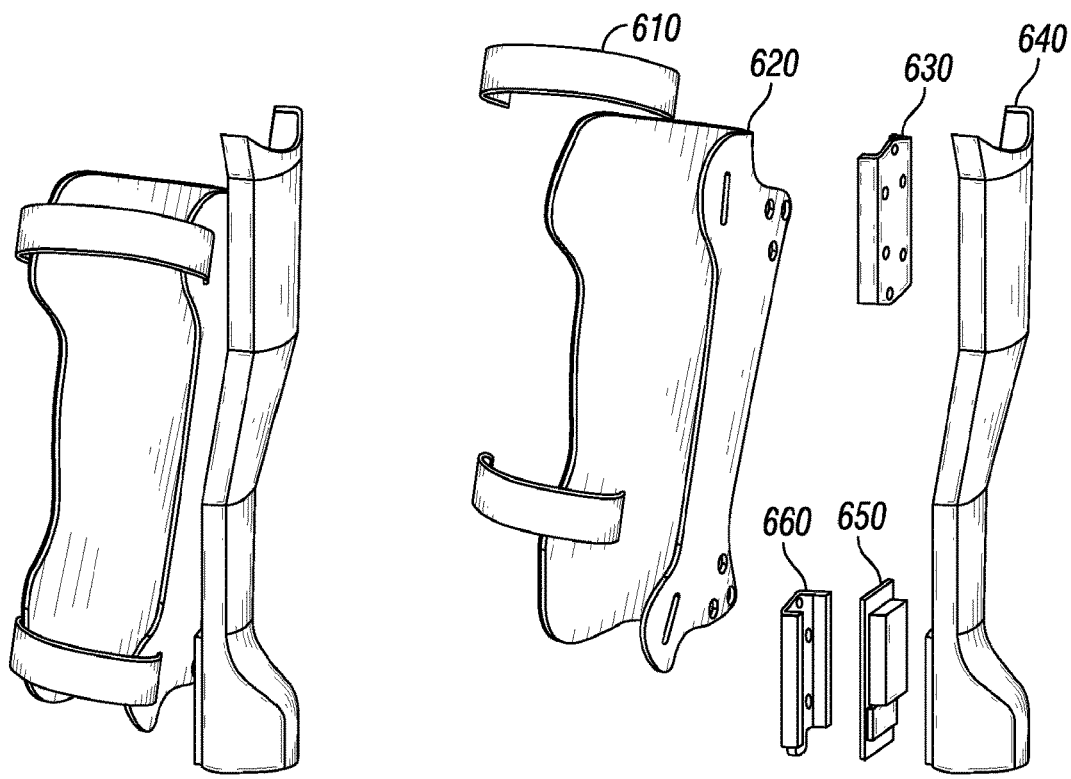
FIG. 30A  FIG. 30B

CUSTOMIZABLE ORTHOTIC/PROSTHETIC BRACES AND LIGHTWEIGHT MODULAR EXOSKELETON

RELATED APPLICATIONS

This application is a national stage filing under 35 U.S.C. 371 of PCT/US2017/037457, which claims the benefit of U.S. Provisional Patent Application No. 62/349,921 filed on Jun. 14, 2016, which is incorporated herein by reference.

FIELD OF THE INVENTION

This invention relates to a customizable orthotic/prosthetic braces and lightweight modular exoskeleton.

BACKGROUND OF INVENTION

Almost a million people in the US alone use a lower limb orthosis. Orthosis devices range in function and application, but a couple features are the same through all systems—an orthosis must interface with the user in a comfortable and safe manner and the orthosis must provide some support to the user. These vary from custom foot insoles to full leg frames attached to patients with customized braces. Systems with rigid frames across joints often interface with the user through a custom formed brace that matches the geometry of the individual's leg.

Current technology takes advantage of a few different methods for constructing these custom braces. The traditional method relies on hands-on plaster casting and other hand methods while modern technology has added 3D scanning and computer controlled 3D forming to the list of available tools. These current orthopedic brace manufacturing methods are largely dependent on hand methods that are prone to geometric errors requiring many iterations to make a usable form. Additionally the interface between the structural component of the orthosis and the user interface brace often requires mechanical fasteners which increase size and weight and concentrate stresses on the plastic or composite braces causing localized failure points. Just attaching metal hardware to braces for the structural support greatly limits the options for location and geometry of the structure or dramatically increases cost. A more modern technique utilizing 3D scanning may utilize expensive CNC machines to craft the positives and orthotic.

There are many different causes for lower limb motor impairment including spinal cord injuries, strokes, traumatic brain injuries and others. Loss or impairment of motor function can take a negative toll on individuals causing physical, mental and monetary hardships. Decreased mobility has been linked to higher blood pressure, shorter life expectancy, social stigma and increased rates of depression. Walking is cited as one of the primary goals of rehabilitation due to the physiological and social implications.

Improved orthotic/prosthetic braces, joint actuators, and lightweight exoskeletons are desired.

SUMMARY OF INVENTION

In one embodiment, improved customizable orthotic/prosthetic braces and a lightweight modular exoskeleton may aid individuals with lower limb motor impairment. These customizable orthotic/prosthetic braces improve the strength and rigidity of such braces without a weight penalty. A structural frame is embedded between an inner shell and outer shell, which comprise materials that are easily moldable to conform to a user's limb.

In one embodiment, a lightweight modular exoskeleton system provides multiple joint actuators, which are designed to be modular, that act as the active joints (e.g. hips, knees, and ankles) of the exoskeleton. Additionally, the exoskeleton also provides passive joint(s) for inversion/eversion of the legs and feet. Foot, crutch, and hip assemblies may also be provided for the exoskeleton. Further, the actuators, foot assembly, and hip assembly may be connected together utilizing thigh and shank brace assemblies, which may correspond to the customizable orthotic/prosthetic design.

In one embodiment, a joint actuator provides an electric motor, wherein the shaft is arranged parallel to a vertical axis. Further, a right angle gear assembly may be coupled to the motor, wherein the right angle gear assembly translates rotation of the motor into rotation of an output shaft of the right angle gear assembly about a joint axis of rotation. An input arm may be secured to the right angle gear assembly, wherein the input arm provides a first attachment arm. An output arm may provide a second attachment arm, and a strain wave gear assembly may couple the input arm to the output arm.

The foregoing has outlined rather broadly various features of the present disclosure in order that the detailed description that follows may be better understood. Additional features and advantages of the disclosure will be described hereinafter.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 5A-5B show side views of an exemplary shin brace;

FIGS. 5C-5D show views of an exemplary thigh brace;

FIG. 10 is a degree of freedom diagram for an exoskeleton system;

FIGS. 11A-11B show lateral (left) and medial (right) view of the modular joint actuator;

FIGS. 20A-20B respectively show strain estimations (50 Nm torque applied to the input), and a tensor map of principle components of stress;

FIG. 28 shows an instrumented shoe assembly;

FIG. 29 shows a shank assembly of the exoskeleton;

FIGS. 30A-30B show and assembled and exploded view of components of the shank assembly.

DETAILED DESCRIPTION

Figure 1:
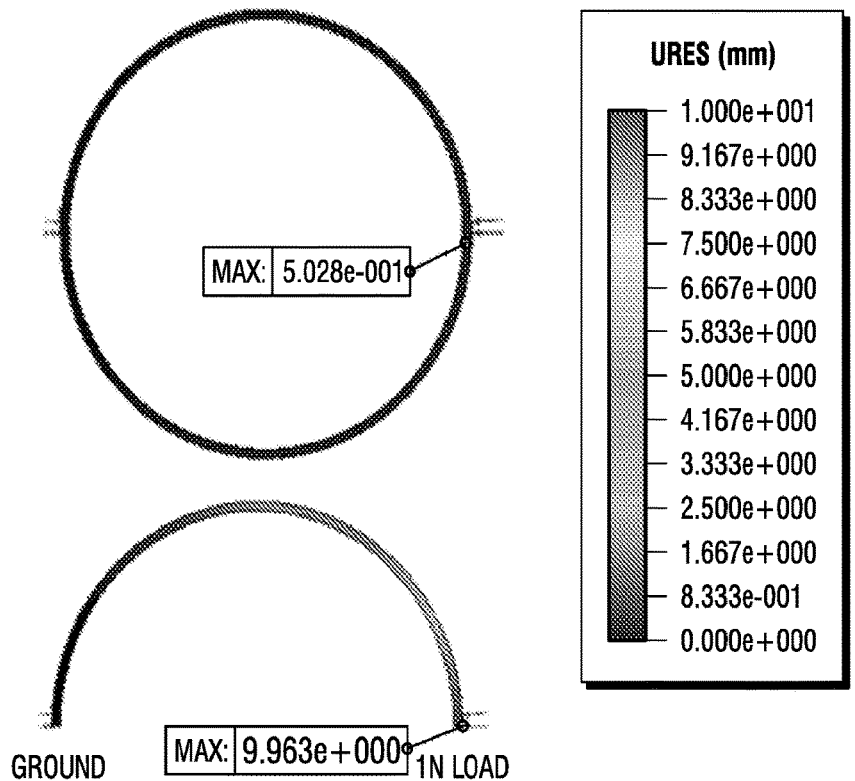
FIG. 1 shows varying displacement given the same loading conditions for a closed ring versus an open arc.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

Customized Orthotic/Prosthetic: Open Form Vs. Closed Form

For open forms, such as a brace that only covers the posterior portion of a limb, the overall rigidity is greatly reduced. As advances are made in powered orthoses and continuously adjustable prosthetic sockets, these open forms are becoming more prevalent and the load requirements are becoming more stringent. Under the same loading conditions, the closed feature undergoes 5% the displacement of the open feature for this thin walled tube (an approximate geometry of most orthotic or prosthetic interface devices.

FIG. 1 shows varying displacement given the same loading conditions for a closed ring versus an open arc. A few different solutions currently used are to employ a heavier or thicker material, make the material thicker in high load areas, include bi-lateral hardware support or add external reinforcing components. All of these solutions come at the cost of increased weight and potentially a limitation on the actual configuration of the reinforcement.

Orthotic/Prosthetic

The proposed customizable orthotic or prosthetic involves reinforcing the composite form of the brace or socket with a lightweight, embedded, custom made reinforcement component. Rather than relying on the intrinsic additional strength of the reinforcing member, the added structural rigidity will come from the change in geometry of the composite material from a relatively flat form to a three dimensional form. This reinforcing member can be made from any suitable lightweight material, such as, but not limited to, a matrix of ABS plastic. It can include locations for external hardware attachment. The geometry of the reinforcement can be directly related to the geometry of the underlying limb or residual limb as well as the type of loading that the component will undergo.

The following description includes a nonlimiting specific case study of the application for the orthosis or prosthesis reinforcement method that illustrates the intended use of the device. However, it shall be understood that such example is not all encompassing in the scope of its possible applications.

Figure 2:
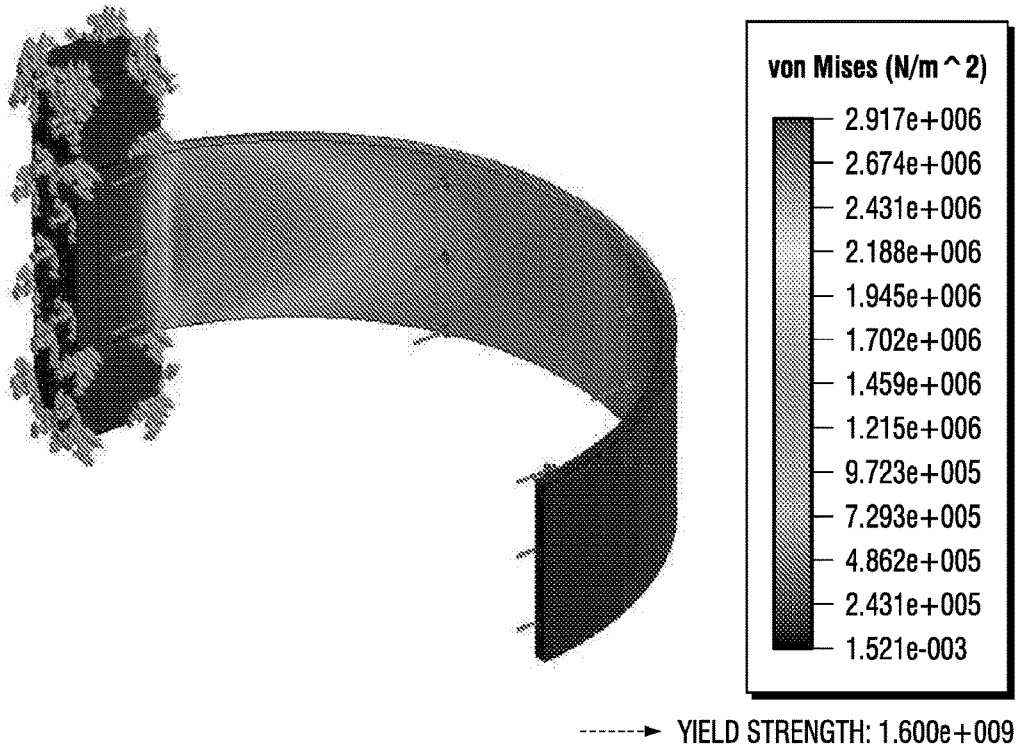
FIG. 2 shows simulation of stresses on a simulated carbon fiber brace with a fixed vertical beam and evenly distributed loading across the face of the brace.
Figure 3:
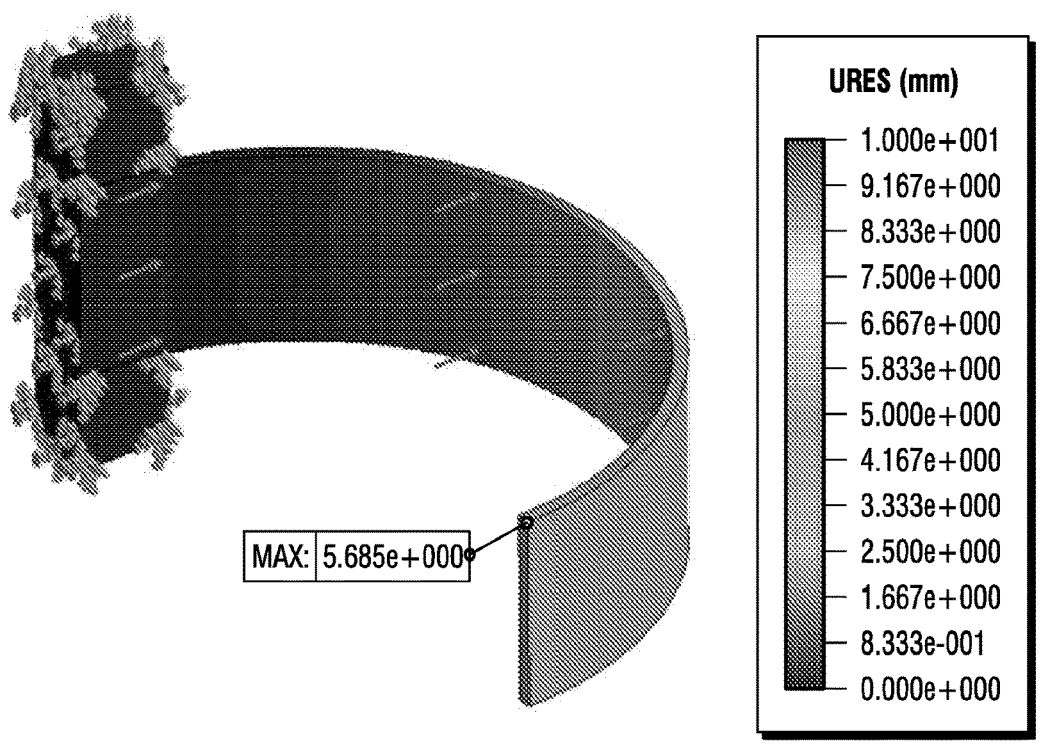
FIG. 3 shows simulation of displacement on the simulated carbon fiber brace.

Current exoskeletons have undergone changes in design that impose different loading conditions on braces. The applied loading from the user may be distributed across the brace, but the interaction forces are concentrated at the point of connection between the brace and the exoskeleton. This creates a loading scenario as shown in FIG. 2 and FIG. 3 with high deflection at the medial edge and high stress near the connection point. FIG. 2 shows simulation of stresses on the simulated carbon fiber brace with a fixed vertical beam and evenly distributed loading across the face of the brace. A nominal loading of 1N is used to demonstrate the location of the stress. FIG. 3 shows simulation of displacement on the same simulated carbon fiber brace as FIG. 2. Such a loading scenario has the potential to maximally deflect the brace at the most medial points and apply strain to the connection point with the frame.

The improved orthotic/prosthetic discussed herein intends to address two main concerns with the current state of the art: customize braces for exoskeletons that match the user's limb geometry and create a brace that optimizes strength and rigidity according to the loading requirements of the exoskeleton. Thus, the precision exoskeleton brace systems discussed herein are personalized to the wearer's limb geometry.

Brace Design

Figure 4:
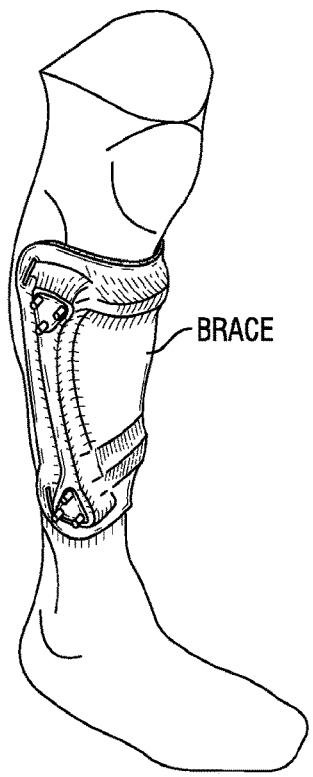
FIG. 4 shows a nonlimiting example of an exoskeleton shin brace in relation to a leg.

An example of a completed braced formed by such process is shown in FIG. 4, which shows an exoskeleton shin brace in relation to leg.

The design features of interest for braces discussed herein may include:

Carry axial loading between exoskeleton attachment points.

Minimize deflection of the medial edge of the brace. In some embodiments, it may be desirable to minimize deflection to less than 1 mm while under maximum loading from the exoskeleton/user interaction forces.

Include load distribution points for attachment locations to an exoskeleton framework.

Include reinforcement points for attaching a removable posterior panel.

The general design requirements are met with the following features as seen in FIGS. 5A-5B, which show side views of the brace:

Vertical support beam 1 between exoskeleton attachment points 3.

Longitudinal or horizontal support ribs 2 to minimize deflection of the medial edge.

Hardware platform that provides load distribution points.

Attachment point(s) 4 to allow a removable opposing panel to be attached.

While the design requirements are shown for the shin brace in FIGS. 5A-5B, it shall be understood by one of ordinary skill in the art that the same principles apply to any other brace, such as a shank, hip, or thigh brace. In some embodiments, frame comprises a vertical support beam, a top horizontal support rib, and a bottom horizontal support rib. Notably, some embodiments of the frame provide only minimal structural support or rigidity to the brace, whereas the frame may provide significant structural support in other embodiment. However, the frame provides a desired shape for the brace that supplies the desired structural support or rigidity for the brace. In some embodiments, the brace also comprises an inner layer and outer layer with the frame sandwiched between the inner and outer layers. The inner and outer layers conform to the shape of the frame embedded between the layers. Due to the shape and material, the inner and outer layers provide a desired level of structural rigidity. The brace may also comprise at least one actuator attachment for coupling the brace to a joint actuator. For example, hip braces may require actuator attachment(s) for the hip joint(s), whereas thigh and shank braces may require actuator attachments at both ends (e.g. for hip and knee joints or knee and ankle joints respectively). The brace may also comprise securing attachment(s) that facilitate a limb of a user being secured in the brace, such as straps or a posterior brace.

Further, while the shin and other braces shown are anterior braces, it shall be recognized by one of ordinary skill in the art that posterior braces providing the abovenoted design features are also possible. FIGS. 5C-5D show views of a thigh brace (posterior), which also provide the abovenoted design requirements. In contrast to the brace in FIGS. 5A-5B, the thigh brace shown in FIGS. 5C-5D is 3D printed with carbon fiber reinforce nylon. The processes for forming these braces are discussed further below.

Figure 6:
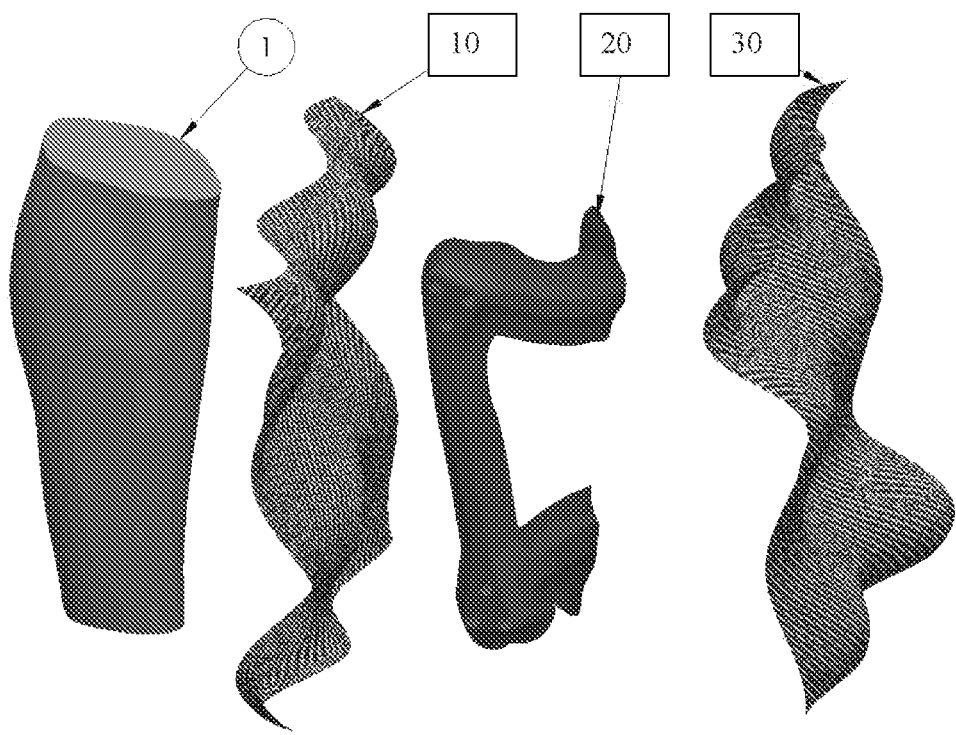
FIG. 6 shows a mold and unassembled view of an inner shell, embedded frame, and outer shell of an brace.

FIG. 6 shows a general structure of a brace for an exoskeleton discussed further herein. While FIG. 6 is shown as a shin brace, it will be recognized by one of ordinary skill in the art that features noted may be present in other braces (e.g. thigh, hip, etc.). The brace assembly of the final structure comprises three main components including the support hardware, namely the inner layer or shell 10, the embedded frame 20, and the outer layer or shell 30. As shown, the mold 40, e.g. thigh, shin, hip, etc., represents the shape that the desired brace may conform to.

Figures 7A, 7B:
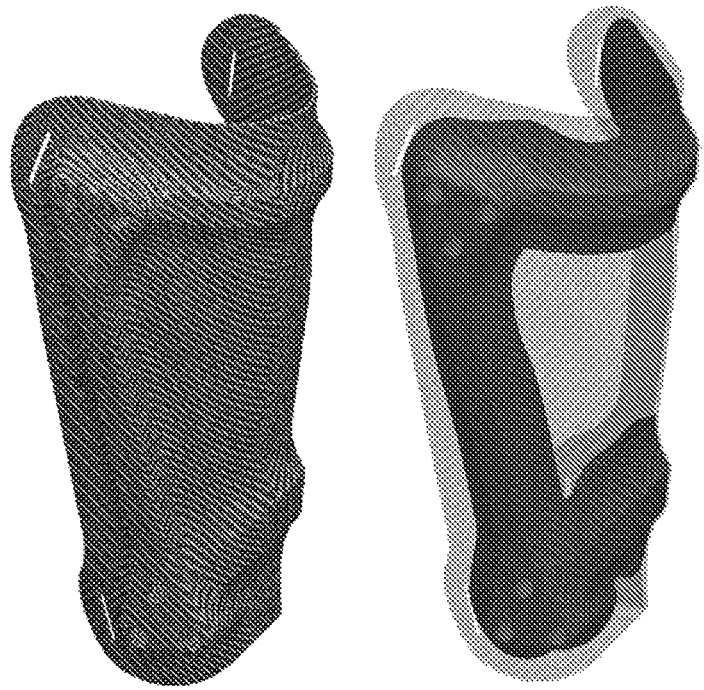
FIG. 7A-7B respectively show an assembled view of a brace where an embedded frame is not visible, and a transparent view of inner and outer shells so an embedded frame is visible.

In a nonlimiting example, the inner 10 and outer 30 shells may be carbon fiber cloth, which remains flexible until the epoxy and curing steps to allow molding. The embedded frame 20 provides geometry for the shells to become the vertical brace 1 and longitudinal support ribs (e.g. see 2 in FIGS. 5A-5B) to add the structural rigidity desired. As noted previously, the embedded frame 20 may be nonstructural (meaning frame 20 provides a minimal rigidity), and as such, may be hollow in some embodiments. As a nonlimiting example, the embedded frame 20 may be formed from ABS. After assembly, added epoxy, curing and trimming the final brace would look like FIGS. 7A-7B. As shown in FIG. 7A, the inner and outer shells surround the embedded frame so it is not visible, where FIG. 7B shows the frame embedded between the inner and outer shells.

The braces discussed above may be formed in a variety of manners; however, two nonlimiting embodiments are discussed herein. In one embodiment, the intended design includes a shell (e.g. carbon fiber) formed over a 3D printed framework (e.g. ABS plastic) that creates the appropriate geometry for meeting the loading requirements, provides reinforced locations for attaching the exoskeleton frame to the brace, and optimizes the strength to weight ratio of the structure for improved exoskeleton performance.

An illustrative nonlimiting example of a suitable process for constructing such a brace may include the following steps:

(a) Obtain a mold or form of a patient's limb (e.g. leg) for the brace construction utilizing any suitable method, such as, but not limited to, 3D scanning and printing, plaster casting, or the like.

(b) Identify the primary loading directions and areas that need reinforcement according to the intended use of the orthosis, such as hardware attachment points. As a nonlimiting example, the load analysis may be performed using finite element analysis or the like.

(c) Design a framework (or embedded frame) over the geometry of the 3D scanned leg geometry that meets the reinforcement requirements. It should be noted that the framework may be non-structural and provides desired reinforcement via changes to the geometry of the inner shell, outer shell, or both.

(d) 3D print the framework, such as with sparse ABS plastic or nylon.

(e) Apply layers on the patient's leg form to create an inner shell. For example, half the intended layers of carbon fiber cloth may be applied to the leg form.

(f) Insert the framework with reinforced design features onto the inner shell.

(g) Apply layers on the framework to create an outer shell. For example, the outer layers of carbon fiber cloth may be applied onto the framework.

(h) Add any hardware that is intended to be incorporated in the brace.

(i) Merging the inner shell, framework, and outer shell to form the orthotic or prosthetic brace. As a nonlimiting example, the form may be vacuum bagged and flood with epoxy to create the final geometry, and allowed to cure and cut to the intended final shape.

In yet another embodiment, a brace may be 3D printed. The initial steps discussed for the process above (a)-(c) may also be performed in this embodiment, but subsequent steps vary from the prior embodiment. Rather than only 3D printing the framework in steps (d) and proceeding to step (e) involving a carbon fiber layup on the surface of the 3D printed framework, the entire brace can be 3D printed with multiple materials in step (d). In some embodiments, the 3D printed core of the brace may be a structural material (e.g. carbon fiber), and the surrounding material may be any suitable material that can maintain the desired shape of the brace (e.g. nylon, carbon fiber, or the like). In a nonlimiting example such as the brace shown in FIGS. 5C-5D, a 3D printed nylon brace is reinforced by a simultaneously printed carbon fiber core. As shown, one of the benefits of 3D printing the entire brace is that the structural materials (e.g. carbon fiber) can be selectively applied to the load bearing areas or components as an outer layer, inner layer, or both. In other words, the outer and inner layers do not need to cover the entirety of the brace, thereby avoid material waste. In the example shown, the vertical frame to which the joints attach and the ribs that extend from the embedded frame are reinforced with carbon fiber (dark grey regions) making them stiff and strong compared to the relatively tough and flexible nylon that matches the shape of the pilot's leg.

As the embodiments of the brace discussed above are customized to a particular user, the braces obviate the need for adjustable length features in an exoskeleton system, thereby also avoiding the added weight of such adjustable features. In some embodiments, pressure sensor(s) may be positioned on or embedded in the brace to provide detection of brace pressure. The following examples are included to demonstrate particular aspects of the present disclosure. It should be appreciated by those of ordinary skill in the art that the methods described in the examples that follow merely represent illustrative embodiments of the disclosure. Those of ordinary skill in the art should, in light of the present disclosure, appreciate that many changes can be made in the specific embodiments described and still obtain a like or similar result without departing from the spirit and scope of the present disclosure.

The theoretical foundation of this design is that it is stronger and lighter weight than an equivalent design using existing assembly methods. This can be compared to two other conditions—a brace made of the equivalent carbon fiber or a brace with the equivalent stiffness properties using only carbon fiber. To further emphasize the contribution of the geometry versus the strength of the inner core, these calculations are conducted assuming that the 3D printed form does not contribute to the strength of the system and is approximately 10% the density of solid ABS (a reasonable estimate for a sparse printed lattice.)

Figures 8A, 8B, 8C:
FIGS. 8A-8C respectively show cross section comparisons of (a) double layer, (b) solid form, and (c) open form configurations.

FIGS. 8A-8C respectively show cross section comparisons of (a) double layer, (b) solid form, and (c) open form configurations. The following results are based on using similar material properties for each from an estimation of the material properties of a bi-weave, epoxy reinforced carbon fiber:

| Material Properties | |
|---|---|
| Elastic Modulus | 2.0 GPa |
| Poisson's Ratio | 0.394 |
| Density | 1020 kg/m^3 |

The simulations were run using SolidWorks Simulation, fixing one end and applying 1N on the other end toward the center of the brace. The mesh used the standard mesh using four Jacobian points, 2.58 mm elements with a 0.13 mm tolerance. Results are given as the maximum displacement of a node relative to its original location in space (relative to the fixed geometry) and the maximum von Mises stress calculated.

| Results | | | |
|---|---|---|---|
| Configuration | Weight [g] | Max Displacement [mm] | Max von Mises Stress [MPa] |
| Double Layer | 7.9 | 9.96 | 3.80 |
| Solid Form | 14.6 | 1.07 | 1.00 |
| Open Form | 8.7 | 1.08 | 1.15 |

As can be seen from the results of the simulation, the open form "reinforcement" is almost as strong (87%) as the solid form with the same displacement but much lighter (60%). Compared to the simple double carbon fiber layer with no form or reinforcement, the open form reinforcement is much stronger (330%) and only slightly heavier (110%). While there will always be a tradeoff between strength and weight, this solution seems to maximize the strength to weight ratio.

The novel method of constructing joints for orthoses or prostheses presented above can allow for high strength, lightweight, customized form (i.e., personalized) and strength components. The construction process follows similar steps to current orthosis or prosthesis construction methods but includes the key internal framework that creates the geometry for taking full advantage of the strength of the composite form.

Lightweight Exoskeleton

The exoskeleton system described herein is a novel device that enables individuals with loss or impairment of lower limb motor function to regain mobility for either the purpose of rehabilitation or for improving accessibility and general health. The orthotic/prosthetic braces discussed above may be utilized with or without this improved exoskeleton systems discussed herein.

Exoskeleton Design

Figure 9A:
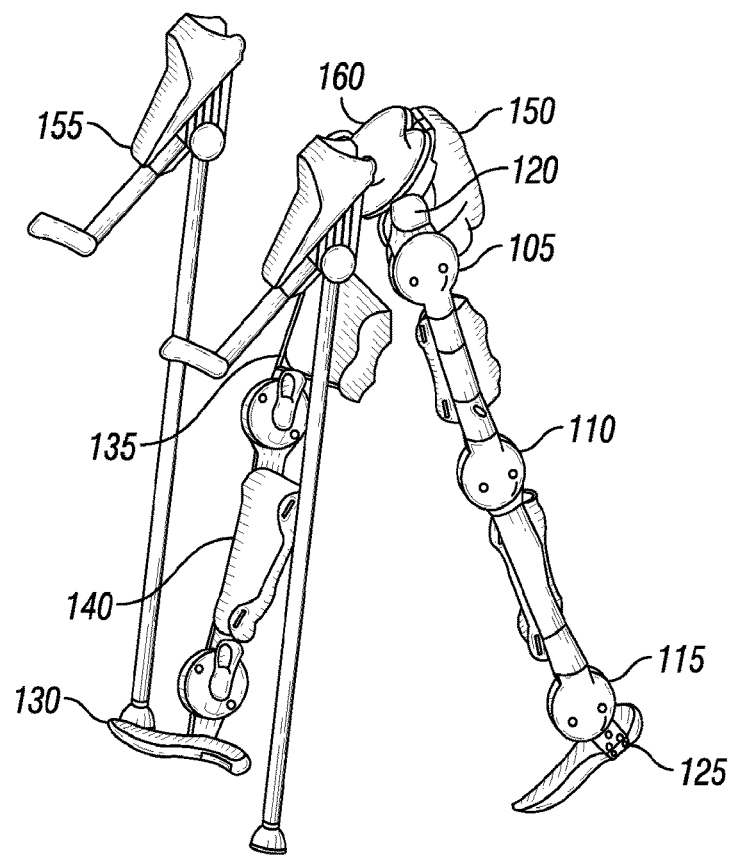
FIGS. 9A-9D respectively show an exemplary exoskeleton system and views of additional embodiments.
Figure 9B:
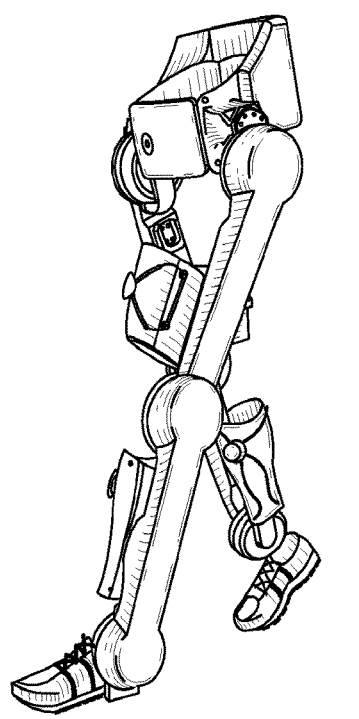
Figure 9C:
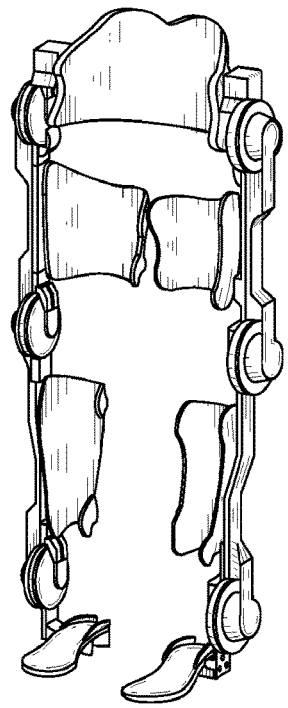
Figure 9D:
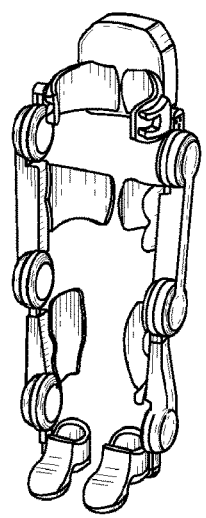

FIG. 9A shows an embodiment of an exoskeleton system. FIGS. 9B-9D show further nonlimiting examples of an exoskeleton system. Note that anterior braces (shown in FIG. 9B) are not shown in some embodiments for clarity. Further, FIG. 9D shows design of the exoskeleton system allows the system to easily be scaled as desired to accommodate children or the like. The exoskeleton system may be a lower limb exoskeleton is a powered mechanical device that attaches to a user's legs and transmits power from the mechanical system to the user in order to actuate the user's limbs for tasks, such as, but not limited to, walking, climbing stairs, walking on ramps and other activities that the user would not otherwise be able to accomplish due to paralysis or a similar mobility limiting condition.

FIG. 10 is a degree of freedom diagram for the main exoskeleton structure of an exoskeleton system. In some embodiments, an exoskeleton system may comprise a main unit, a plurality of actuators or joint actuators (e.g. hip, knee, ankle, or combinations thereof), and a plurality of brace assemblies (e.g. hip, thigh, shank, or combinations thereof). The main unit may provide power and control for the system. The joint actuators (discussed further in discussion below) are modular, powered joint actuators. The actuators may comprise a motor, first arm, and second arm, which allows the actuator to provide rotary motion between the first and second arm. The brace assemblies (e.g. hip, thigh, or shank, discussed further in discussion below) comprise the brace itself, and may optionally include a housing to protect components of the exoskeleton, one or more controller electronics for a joint, and/or adapter(s) utilized to couple the brace to a joint actuator. Depending on the user's needs, the number of actuators and braces can be modified. As a nonlimiting example, if a user has partial paralysis where only a left leg requires an exoskeleton system, the exoskeleton system may consist of a hip brace assembly, left hip actuator, left thigh brace assembly, left knee actuator, left shank brace assembly, left ankle actuator, and left foot assembly.

In some embodiments, the exoskeleton system may comprise two powered joints or more. It shall be apparent to one of ordinary skill in the art that the modularity of the exoskeleton system allows the system to be easily modified to accommodate targeted joints as desired, such as, but not limited to, a partial system for the left leg, right leg, hips and knee joints only, etc. In some embodiments, the exoskeleton system may comprise six powered joints or more. In some embodiments, the exoskeleton system may comprise four passive joints or more. In some embodiments, the exoskeleton system may comprise powered/passive joints arranged to provide a total of 10 degrees of freedom or more. In some embodiments, the six powered joints include articulation about the exoskeleton user's biological hip joints, knee joints, and/or ankle joints in the sagittal plane. Further, the power joints may represent the joints of the exoskeleton system that provide a powered actuator. In some embodiments, the passive joints include abduction and adduction of the hip joint and/or inversion and eversion of the ankle joint. In some embodiments, in addition to the powered/passive joints discussed above, additional powered or passive joints may be added, such as to allow for mediolateral movement.

Referring to nonlimiting example of an exoskeleton shown in FIG. 9A, the hip 105, knee 110, and ankle 115 joints are powered, whereas the hip socket 120 and foot joints 125 are passive. In some embodiments, the exoskeleton system may comprise foot segment(s) 130, joint actuator(s) 105, 110, 115, leg bracing(s) 135, 140, main unit 150, crutch(es) 155 or a combination thereof. The primary components of the exoskeleton include Foot 130, Leg Brace 140, Thigh Brace 135, hip/waist brace 160, Crutch 155, Power Pack 150, Hip Joint 105, Knee Joint 110, and Ankle Joint 115. Each joint 105, 110, 115 is capable of directly measuring absolute position, voltage to the motor, current to the motor, and the housing temperature. Main unit 150 may provide the power supply (e.g. 12 volt lithium iron phosphate batteries), a battery management system, voltage multiplier, regulators for the control module power supply, master control module/main controller, user interface controls, communication lines for the crutch input, and the like.

While FIG. 9A shows a nonlimiting example of an exoskeleton for both legs, the overall design of the exoskeleton is designed to be modular such that the exoskeleton assembly can be tailored to specific patient needs. It should be understood that the most basic example of an exoskeleton may include a main unit, actuator, and brace assembly. The modularity allows additional actuator(s), brace(s), foot segment(s), crutch(es) or a combination thereof to be added as desired. As nonlimiting examples, this means that actuators can be scaled or eliminated, braces can be reduced or strengthened, and the overall system can meet the size requirements of the patient from a four year old child to an adult with very little alteration to the described design concept (e.g. FIG. 11B).

| Component | Adult | Pediatric |
|---|---|---|
| Motor | 100 W Eci 40 | 70 W EC Flat |
| 90 deg. Gear | 4.125 Spiroid | None |
| Harmonic Gear | 50:1 | 160:1 and 100:1 |
| Power Supply | 1-6 12 V LiFePO$_4$ | 1-4 12 V LiFePO$_4$ |

Mechatronic Design: Primary or Joint Actuator

FIGS. 11A-11B show lateral (left) and medial (right) view of the modular actuator segment 200. The joint actuator (actuator or joint herein) 200 is modular and may at as a joint for various joints in the exoskeleton, such as the hip, knee, or ankle joints. Each actuator 200 comprises an electric motor 210, such as a brushless DC motor, coupled to a ninety degree angle gear (not visible), which may output to a further gear reduction. The motor 210 is fixed to the "input" arm 220 of the joint and the final gear output is fixed to the "output" arm 230 of the joint. In this specific configuration, the motor is in line with or parallel to the axis of the limb segment, rather than the axis of the joint. This allows for scaling of the drive components without drastically affecting the overall ergonomics of the actuator.

Figures 12A, 12B, 12C, 12D:
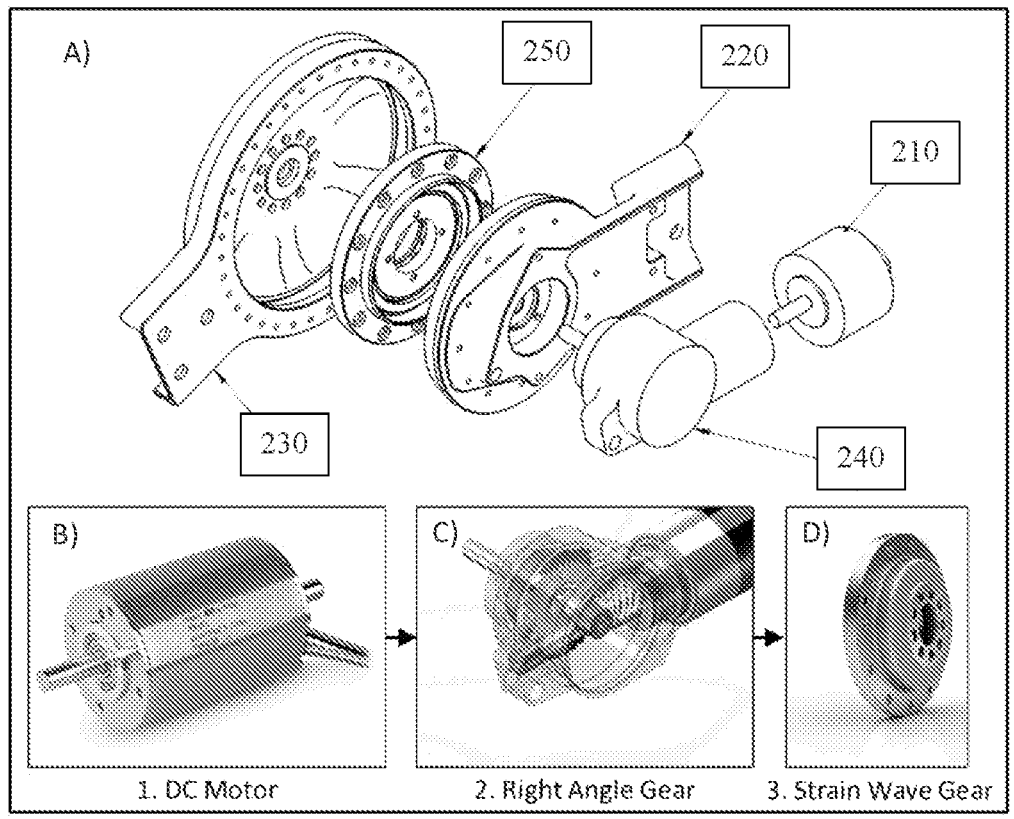
FIGS. 12A-12E respectively show an exploded view of primary actuator components, individual views of the motor, right angle gear, and strain wave gear assembly, and an overall width of an actuator assembly.

FIG. 12A shows an exploded view of an exemplary actuator 200, particularly of the primary components including: motor 210, right angle gear assembly 240, strain wave gear 250, input arm 220, and output arm 230. FIGS. 12B-12D respectively show individual views of the motor 210, right angle gear assembly 240, and strain wave gear 250. As noted above, it is preferable to have the motor is in line with or parallel to the axis of the limb segment. As such, the motor 210 is arranged in the actuator 200 to be approximately parallel with a vertical axis. The right angle gear assembly 240 receives the shaft of the motor and translates rotation of the motor into rotation of an output shaft about a joint axis of rotation. The input arm 220 provides a generally circular body and an attachment arm extending from the circular body that allows the input arm of the actuator to be secured to a brace. A relatively small opening is provided through the circular body of the input arm 220 that allows the output shaft 242 of right angle gear assembly 240 to pass through the arm. The output arm 230 provides a ring shaped body that allows gear(s) and bearing(s) to fit inside the ring. The output arm 230 may also provide an attachment arm extending from the ring shaped body that allows the output arm of the actuator 200 to be secured to another brace, different than brace secured to the input arm. The actuator 200 may also provide an output plate 260 that may be secured to the output arm 230 and prevents dirt, dust, or the like from entering the actuator. The motor and gear selection for the actuators may be based on a desired combination that allowed for the torque and speed requirements desired for a user to perform a number of acts of daily living while minimizing metabolic expenditure. Various activities have different torque requirements and different speed requirements. While the torque and speed requirements can be quantified relative to the requirements of an able bodied individual performing the same tasks, this does not take into account the use of the crutches. This use may be highly dependent on the individual user and a number of variables, including, but not limited to, variables such as comfort with the system, standing balance, reliance on crutches, reliance on railings, etc. The high degree of unpredictability led to designing for the worst case scenario, where the user would be dependent on the exoskeleton for one hundred percent of the effort to achieve each given task for a $75^{th}$ percentile man. Speed was determined by estimating that the tasks, such as walking, could be performed at least half as fast as an able bodied individual performing the same task, a metric that is consistent or better than the current state of the art systems available. It was determined that a single motor gear combination could work well for all six powered joints of the exoskeleton. However, it shall be understood by one of ordinary skill in the art that the nonlimiting examples discussed herein may be adjusted due to the specific joint requirements based on the user's height, weight and general use of crutches.

Figure 12E:
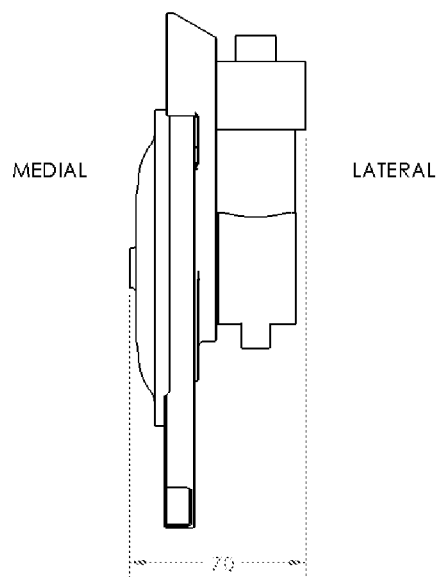

Another important consideration with the actuator is minimizing the size and weight of the system. There is an obvious tradeoff between decreasing the size of the actuator 200 and how much power it can generate. Knowing the output requirements, it becomes an issue of selecting the components and managing the relative position and orientation of the system so as to minimize weight and provide the least intrusion on the user's functionality. Human joints generally have a much slower rotation than DC brushless motors and relatively high torque requirements. Another consideration is minimizing the lateral protrusion of the actuator 200 from the user's body. The solution to both these considerations involves using a thin, lightweight, high reduction wave gear set 250 in tandem with a right angle gear assembly 240. In some embodiments, the reduction wave gear set 250 may be a strain wave gear assembly or harmonic drive, which may provide speed reduction and/or an increase in torque. In some embodiments a combination of a motor, harmonic drive, and spiroid gear may be utilized. As a nonlimiting example, a Harmonic Drive® wave gear set may be used with a spiroid gear head coming from a 100W ECi-40 Maxon® motor. The overall width of an illustrative hardware assembly for this combination is 70 mm as shown in FIG. 12E. In some embodiments, the width or thickness of the actuator may be 100 mm or less. In some embodiments, the width or thickness of the actuator may be 70 mm or less. In some embodiments, the reduction gear set 250 may be a planetary gear set, such as an anti-backlash planetary gear set.

The ECi-40 motor is a small, powerful package with high efficiency. The right angle gear head allows the motor to be oriented along the long axis of the limb, and thus the lateral width of the actuator limited by the diameter of the motor rather than the length. A broader selection of motors with higher length to diameter ratios exists, and the exoskeleton system is in no way limited to particular motor brand or type. Also, since the motor is rotating at high speeds relative to the joint, minimizing the moment of inertia about the axis of rotation for the motor can improve the performance of the overall joint. In this case, a longer, narrower motor has the advantage over a shorter, wider motor because the rotating mass is closer to the axis of rotation.

In some embodiments, the right angle gear assembly 240 on the motor uses a spiroid gear tooth design which decreases noise, improves the efficiency of the joint and minimizes backlash when compared to other ninety degree orientation gears such as bevel gears or worm gears. As a nonlimiting example, the spiroid gear produces a 4.125:1 speed reduction.

Figure 13A:
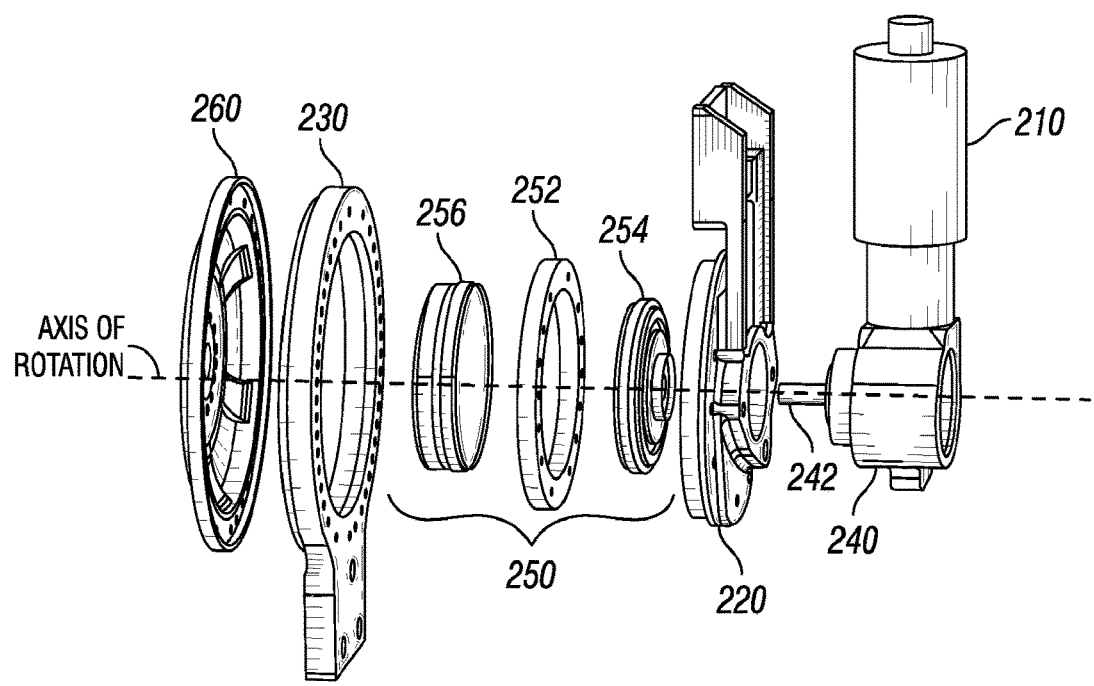
FIGS. 13A-13B respectively show an exploded view of an illustrative example of a joint actuator, and linked component groups of an actuator.
Figure 13B:
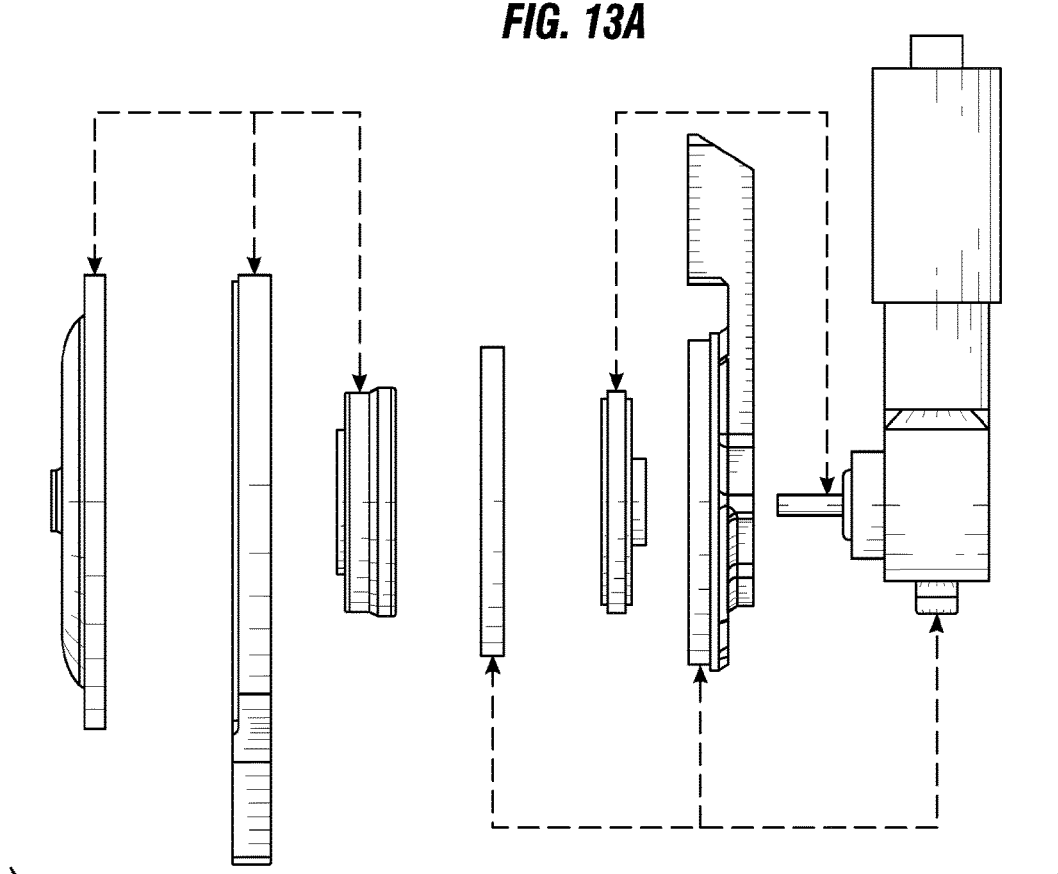

The output of the right angle spiroid gear is coupled to the strain wave gear assembly (or strain wave gear herein) 250 (e.g. 50:1). A strain wave gear 250 allows for a very narrow form, high gear/speed reduction with minimal backlash. FIGS. 13A-13B respectively show an exploded view of an actuator and linking of actuator components. The shaft of the motor (not shown) is arranged perpendicular to the axis of rotation for compactness. The axis of rotation for the actuator 200 is parallel to the output shaft 242. An illustrative example of a strain wave gear 250 (in relation to an actuator 200) which comprises three components: ring spline 252, wave generator 254, and strain wave spline 256. The ring spline 252 is fixed to the "input" arm 220 of the joint. The wave generator 254 is fixed to the output shaft 242 of the 90 degree gear assembly 240—the head of which is fixed to the same "input" arm 220 of the joint. Thus, as shown in FIG. 13B, the motor 210, right angle gear assembly 240, input arm 220, and/or ring spline 252 may be considered to be a first group of linked components. The output shaft 242 of the gear assembly 240 and/or wave generator 254 may be considered to be a second group of linked components. The strain wave spline 256 is fixed to the joint "output" arm 230. Further, the strain wave spline 256, the output arm 230, and/or output plate 260 or may be considered to be a third group of linked components. When the eccentric wave generator 254 rotates, the strain wave spline 256 deflects and advances one tooth at a time around the ring spline 252 for every full rotation of the wave generator. Each group of linked components may be coupled together in a manner that causes the linked components to rotate together. For example, output shaft 242 and wave generator 254 ($2^{nd}$ group of linked components) may rotate together, while motor 210 & gear assembly 240, input arm 220, and ring spline 252 (the $1^{st}$ group) remains stationary. The rotation of the $2^{nd}$ group causes the output arm 230, strain wave spline 256, and output plate 260 ($3^{rd}$ group) to rotate relative to the $1^{st}$ group (notably at different rate due to gear assembly 250). In the nonlimiting example, strain wave gear 250 may provide a 50:1 ratio between the input to the wave generator 254 and the output of the strain wave spline 256.

Figure 14A:
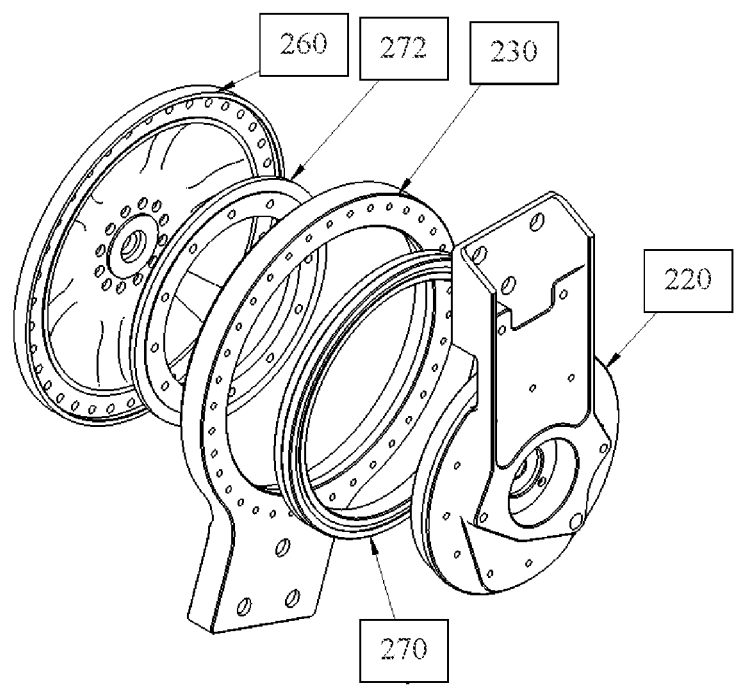
FIGS. 14A-14E respectively show an explode view of an illustrative example of clamping components, clamping components, cross-section A-A, detailed view of section B, and an illustrative example of a cross roller bearing.
Figures 14B, 14C, 14D:
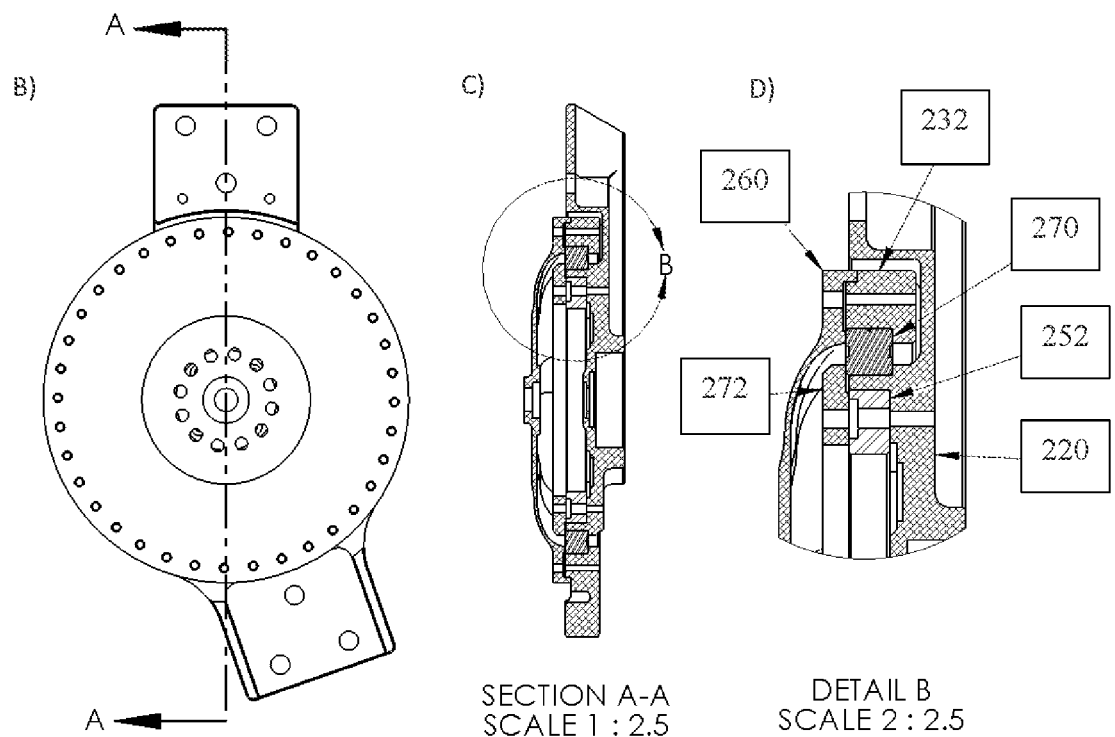
Figure 14E:
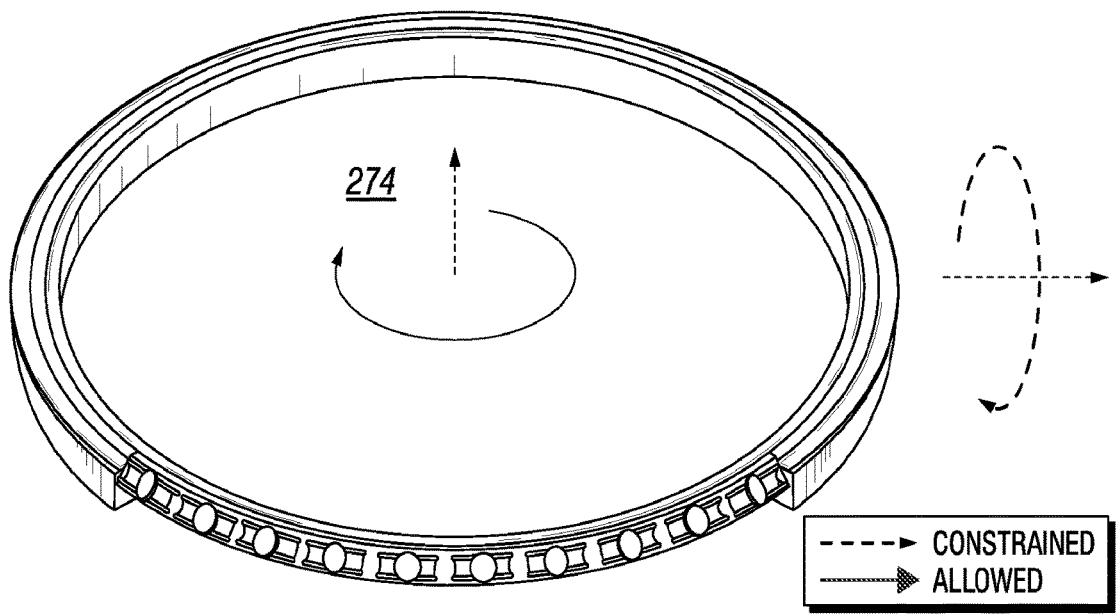

FIG. 14A shows components clamping the cross roller bearing 270, between the input arm 220 and output arm 230 by clamping the inner race of the bearing with the inner race clamping ring 272 to the input arm and the outer race to the output arm with the output plate 260. FIGS. 14B-14D respectively show clamping components, cross-section A-A, and detailed view of section B. Assembly of the cross roller bearing clamping components including: inner race clamping ring 272, output plate 260, output ring 232 (or the ring portion of the output arm 230), cross roller bearing 270, ring spline 252, input arm 220. The primary connection between the input arm 220 and the output arm 230 of the actuator 200, besides the teeth of the gear set, is a cross roller bearing (assembly of bearing not shown). The cross roller bearing may be clamped by the internal diameter ring 272 to the input arm 220 and by the outer diameter ring 232 to the output arm 230. FIG. 14E shows a nonlimiting example of a cross roller bearing assembly 270 and allow/constrained motion. The cross roller bearing uses a series of cylindrical rollers at opposing angles to achieve limiting applied loads in all directions except the primary axis of rotation 274 of the joint. This means that the bearing will handle radial loading (along the axis of the limb segments), lateral loading (along the axis of the joint), and any moments, as illustrated by the other arrows shown, that are not applied around the primary axis of rotation 274 of the joint. A nonlimiting example of a cross roller bearing may be a cross roller bearing from THK America, Inc, Schaumburg, Ill.

With this type of motor and gear combination, a wide variety of power and speed requirements can be achieved depending on the need. This includes, but is not limited to, a motor with different power, different speed or torque ratings, or different gear reduction. Other embodiments may also include using a different type of right angle gear assembly or ninety degree transmission, such as a bevel gear or a worm gear.

Figure 15A:
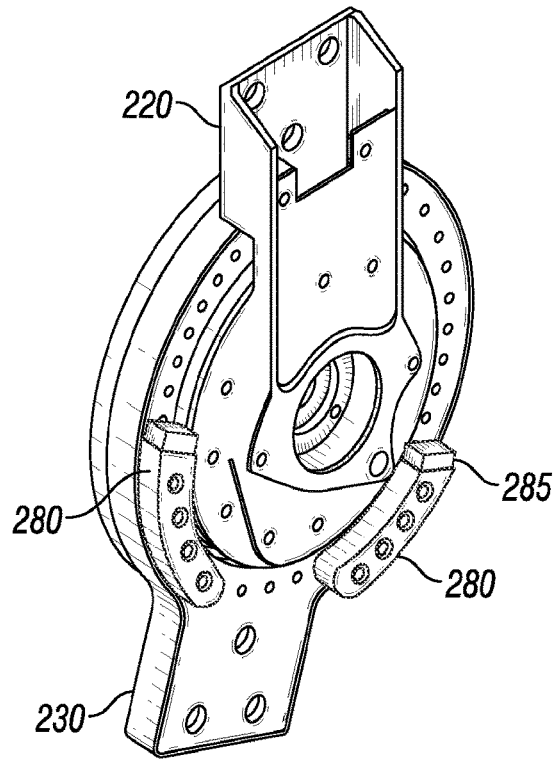
FIGS. 15A-15D respectively shows an illustrative example of hard stops in a joint actuator, and an actuator with hard stops set to different angles for flexion and extension range of motion.
Figures 15B, 15C, 15D:
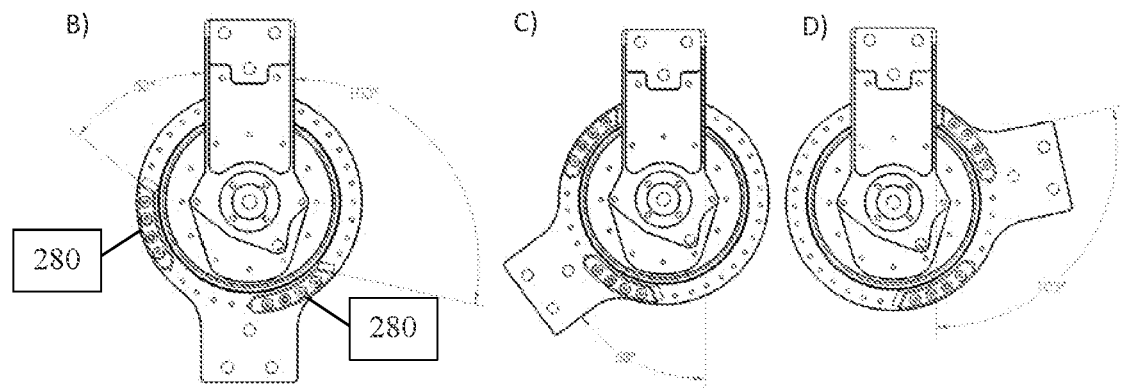

Another important mechanical aspect of the actuator 200 is the adjustable hard stops. FIG. 15A shows an illustrative example of hard stops 280 shown in the actuator assembly. The hard stops 280 may be secured to the output arm 230, and may interface with the input arm 220. These hard stops 280 are simple stops that control the range of motion of the actuator. In some embodiments, the hard stops 280 are blocks that are secured to the output ring of the output arm 230 such that the face of the hard stop makes contact with the input arm 220 when the joint is rotated to the extreme positions of the range of motion. The ROM (range of motion) of an actuator may be defined by the angle between the arms of the input arm 220 and output arm 230 at first extreme position and a second extreme position. FIGS. 15B-15D show an actuator with hard stops 280 set to different angles for flexion and extension range of motion—similar to a sagittal plane hip range of motion. In this particular nonlimiting example, the ROM (range of motion) stops 280 can be placed such that the range of motion can be varied from −120 degrees to 120 degrees in 10 degree increments to suit the particular joint or the particular user's range of motion. However, the spacing of the holes in the ring of the output arm or the geometry of the hard stop relative to the holes may be varied as desired to allow a desired level of adjustability. In some embodiments, the face of the hard stop 280 that may contact input arm 220 includes a rubber bumper to decrease the impulse of the impact if the hard stop were to be engaged. In some embodiments, each hard stop may provide a shutoff mechanism 285 to power off the motor when the hard stops 280 are close to contact or in contact with the input arm 220. As a nonlimiting example, this motor shutoff mechanism may be a trigger pin 285 that is used to press a motor power cutoff button just prior to hitting the stop. When the hard stop trigger pin 285 makes contact with the limit switch, a relay for the motor power supply is deactivated. This ensures that if the motor is uncontrolled or mis-controlled to cause the joint to reach the range of motion limit, power to the motor is cut and the motor will not stall against the hard stop. This prevents the motor from continuing to operate against the hard stop if the cause of the excessive rotation was not resolved.

Figure 16A:
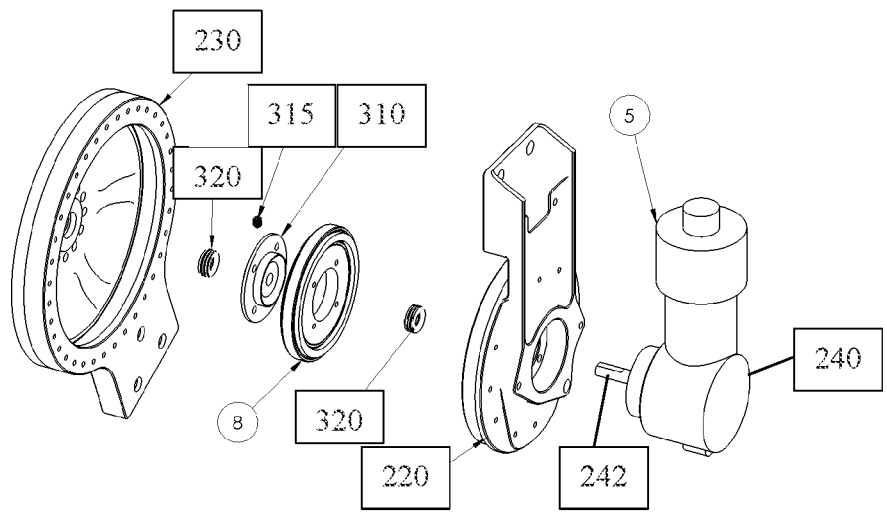
FIG. 16A-16D respectively show an exploded view of an illustrative example of a shaft adapter, a shaft adapter, and corresponding cross section views a shaft adapter.
Figures 16B, 16C, 16D:
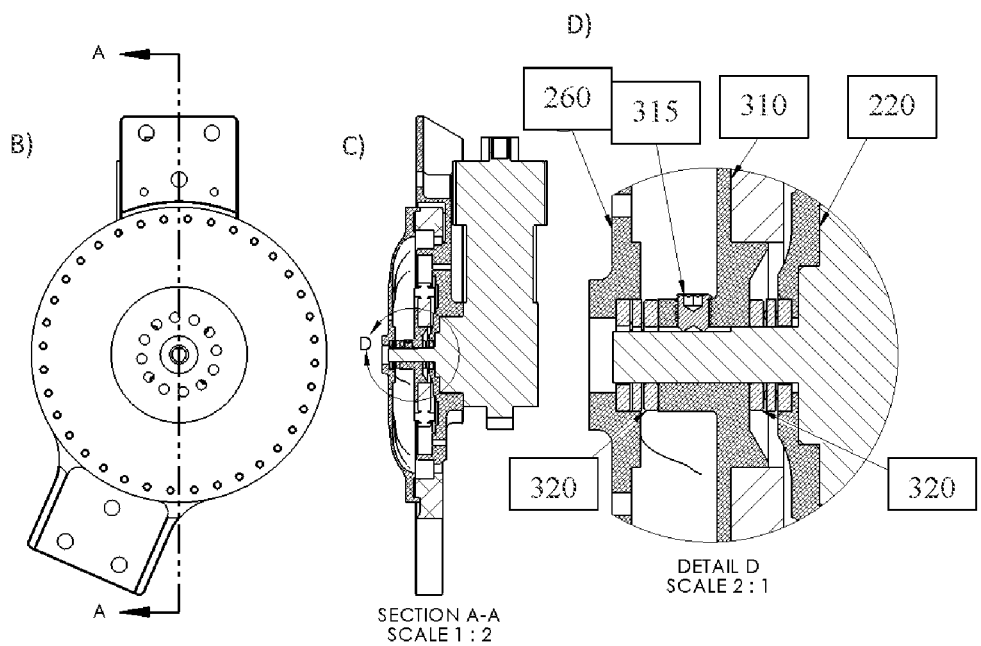

FIG. 16A shows an illustrative example of a shaft adapter. The connection between the output of the spiroid gear and the wave generator may be accomplished with an adapter component. The shaft adapter 310 is mounted to the shaft 242 of the right angle gear 240, and the shaft adapter may be held in place to rotate with the shaft by a set screw 315. The shaft adapter 310 is also attached to (or is a component of) the wave generator 254. Thrust bearings 320 locate the adapter assembly against the arms 230 and 220. The axial position of the adapter 310 on the shaft may also be located by thrust bearings 320 (e.g. two bearings). This is to carry any loading that might be applied by the wave generator 254. The wave generator 254 generates axial loads as it is rotated due to the deflection of the sides. The thrust bearings 320 contain these applied loads, transferring them to the main arm components 220, 230 rather than the gear shaft 242. FIGS. 16B-16D show the shaft adapter and corresponding cross section views. Shaft adapter 310 is located by thrust bearings 320 against the input arm 220 and the output plate 260. A setscrew 315 may be secured in an opening of shaft adapter 310 to engage a flat portion of shaft 242, thereby causing the shaft adapter to rotation with shaft 242.

The input 220 and output 230 arms may have attachment means, such as a bolt pattern, that allows them to be joined to any unique components necessary to assemble the exoskeleton. The components that attached to the actuator 200 vary from joint to joint. For example, the inverting/everting passive components of the ankle are different than the connections to the knee. However, by making the actuator or joint a single modular unit, the same joint actuator 200 can be used in a variety of powered joint locations.

Figure 17A:
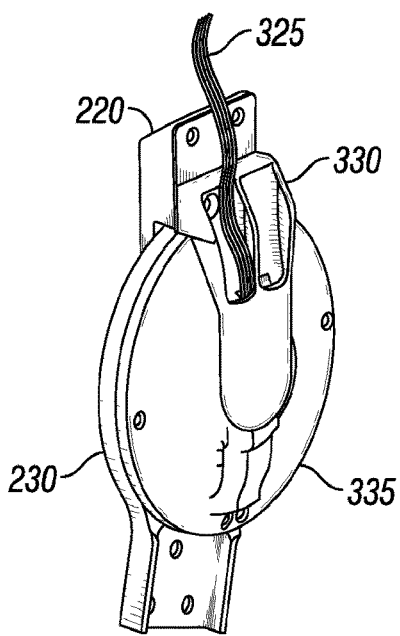
FIGS. 17A-17B respectively show an assembled and exploded view of an illustrative example of an actuator with a rotary encoder.
Figure 17B:
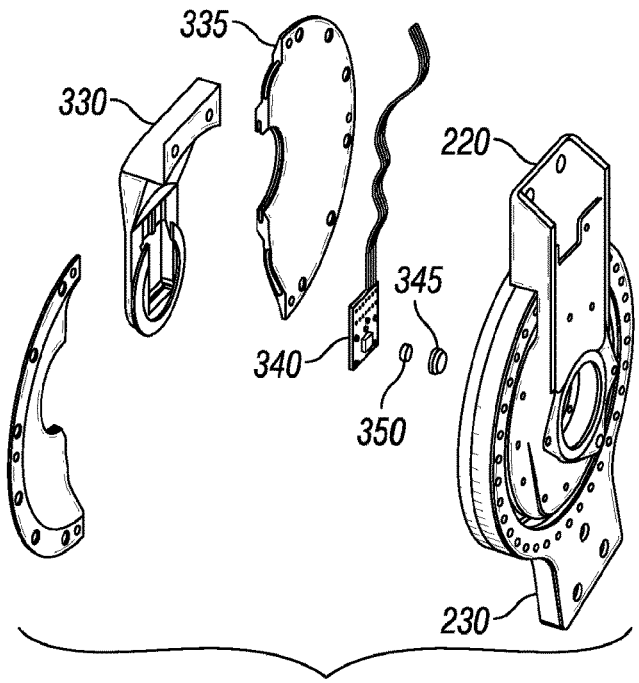

The actuator unit 200 may also contain sensors and outputs that allow it to work as a functional joint in an exoskeleton. Nonlimiting examples of such sensors include: rotary encoder or shaft encoder (e.g. magnetic absolute encoder), voltage meter, current meter, range of motion limit switches, temperature sensor, inertial measurement unit, strain gauges, or the like. FIGS. 17A-17B respectively show a illustrative view and exploded view of an actuator joint. The actuator may provide an input arm 220, encoder communication wires 325, encoder mount 330, encoder mount stabilizing plate 335, and output arm 230. The exploded view from the lateral side in FIG. 17B including: encoder mount 330, encoder mount stabilizing plate 335, encoder chip and PCB 340, input arm 220, output arm 230, magnet mount 345, and magnet 350. As a nonlimiting example, the magnetic absolute encoder is mounted such that the diametric neodymium magnet 350 is fixed to the center of rotation of (or moves with) the output arm 230 of the joint, and the chip and PCB 340 are mounted to a housing connected to (or moves with) the input arm 220 of the joint. The sensor arrangement allows angle information to be detected and provided to desired parts of the system. In a nonlimiting example, the sensor may returns a 12 bit value representing the absolute angle of the joint. This is imperative to effectively measure the angle of the joint at any given time and not rely on any secondary data processing or initialization calibration. This means that even if the system is powered off and restarted, the initial measurement from the sensor will indicate the actual position of the joint.

Voltage and current meters are used to measure the power going to the joint and can be used to implement a power based control algorithm. The meters can also be used for diagnostics to qualitatively measure the efficiency of the joint (and therefore the electro-mechanical state of the joint) and/or to calculate the amount of effort that the user requires from the joint and qualitatively measure their exoskeleton use pattern.

In some embodiments, a temperature sensor may be used to track the thermal behavior of the actuator joint. This is intended as a diagnostic measure to determine if the motor or gears may be over heating. This data can be used as a software shutoff for the joint.

In some embodiments, an inertial measurement unit (IMU) may be provided to measure acceleration, angular velocity, position, or the like for three axes. As a nonlimiting example the IMU may be a nine axis IMU—3 axis accelerometer, 3 axis gyrometer, and 3 axis magnetometer—that can be added to the joint to measure the dynamic behavior of a limb segment. This can be used as a clinical metric determining the motion behavior of limb segments including vibration, stability, lateral motions and other dynamics of interest. It can also be used to inform the overall control loop including impact detection or global orientation.

In some embodiments, each joint has a control board that manages the sensor input, the main controller input and the outputs necessary to actuate the joint, indicate the status and return sensor data to the master controller. Further, each joint may also have a motor controller that actually drives the motor. The joint control board communicates with the overall system control board or master controller and also outputs status indicators, such as RGB LEDs in the joint.

Actuator or Joint Instrumentation

The modular exoskeleton actuator or joint includes instrumentation to inform the overall system controller about the state of the joint. The following table outlines the instrumentation included:

| Instrument | Purpose |
| --- | --- |
| Magnetic absolute encoder | Joint angular position |
| Voltage meter | Motor power consumption |
| Current meter | Motor power consumption |
| Thermometer | Joint hardware temperature |
| Inertial measurement unit (IMU) | Acceleration and angular velocity on three axes |
| Strain gages | Joint output torque |

The encoder, voltage meter, current meter, thermometer, and IMU are discussed above. Further, some embodiments may provide additional sensors described herein, such as strain gauges used to measure the output torque of the actuator or joint.

Measuring joint torque has been done in a wide variety of ways in robotic systems. The commonality of most torque instrumentation is that it measures the deflection of some component in the transmission of the joint. Often a motor shaft is instrumented with strain gauges to determine how the shaft is deflecting under an applied torque.

The transmission of the exoskeleton joint comprise the input arm 220 (which is directly bolted to the Harmonic Drive ring spline 252), the motor 210 stator, the wave generator 254 of the Harmonic Drive rigidly fixed to the output shaft 242, the flex spline 256 of the of the Harmonic Drive rigidly fixed to the output plate 260, and the output plate rigidly fixed to the output arm 230. Measuring the torque in components prior to the Harmonic Drive transmission would require a detailed analysis of the dynamics of the Harmonic Drive. Therefore, components after the Harmonic Drive transmission are more suited for torque measurement.

Figure 18:
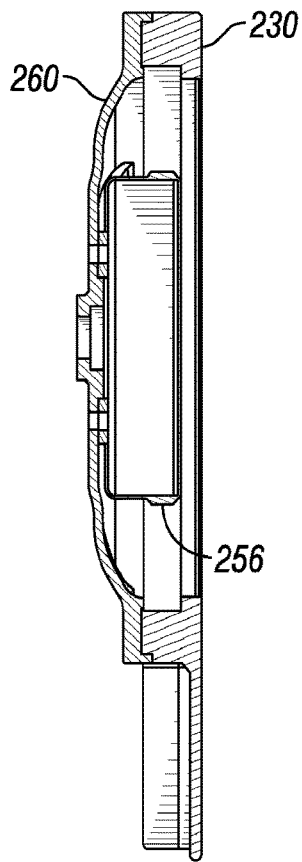
FIG. 18 shows a cross section view of an actuator illustrating transmission of torque in the actuator.
Figure 19:
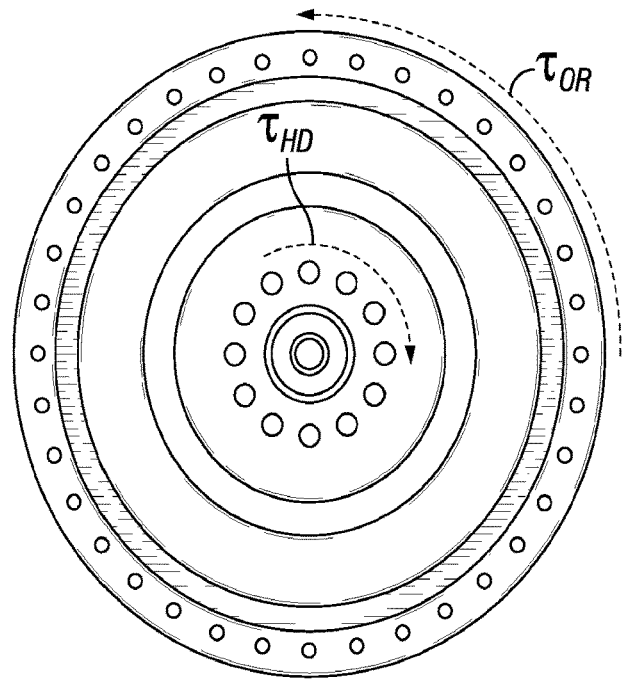
FIG. 19 shows an illustration of the transmission of torque to an output plate and an output ring of an output arm of an actuator.

In this case, the output plate transmits all of the output torque received by the harmonic drive or strain wave gear assembly to the output arm, or more particularly, output torque from the flex spline bolt pattern to the bolt pattern of the output arm. The relatively thin cross section of the output plate also makes it a prime candidate for measuring deflection compared to the output arm. From FIG. 18, it can be seen that the flex spline 256 is bolted to the inner bolt circle of the output plate 260, which is attached to the output ring of the output arm 230 by the outer bolt circle. FIG. 19 shows a free body diagram of output plate 260 with torque from the Harmonic Drive ($\tau_{HD}$) applied to the inner bolt circle and the reaction torque from the output ring applied to the outer circle ($\tau_{OR}$).

Other similar joints try to include specific transmission spokes on which strain gauges can be applied with a bending beam model. However, instead of a bending beam model for the strain gauges, this joint uses a shear model to measure the deflection due to torque on the relatively flat plane of the output plate 260. FIG. 20A shows strain estimations with a 50 Nm torque applied to the input. FIG. 20B shows a tensor map of principle components of stress.

Figure 21A:
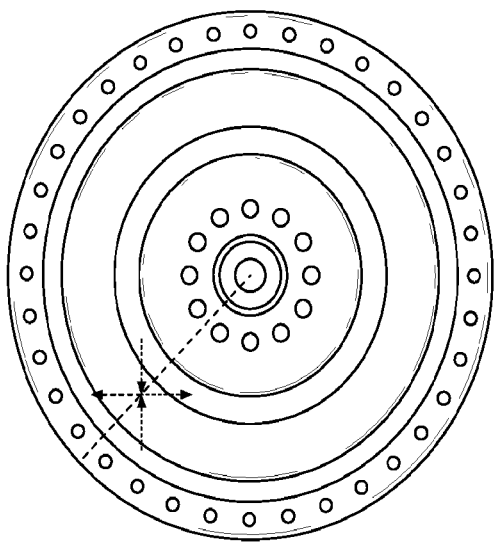
FIGS. 21A-21B respectively show a single node tensor and Wheatstone bridge.
Figure 21B:
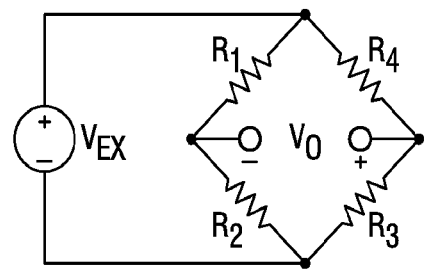
Figure 22A:
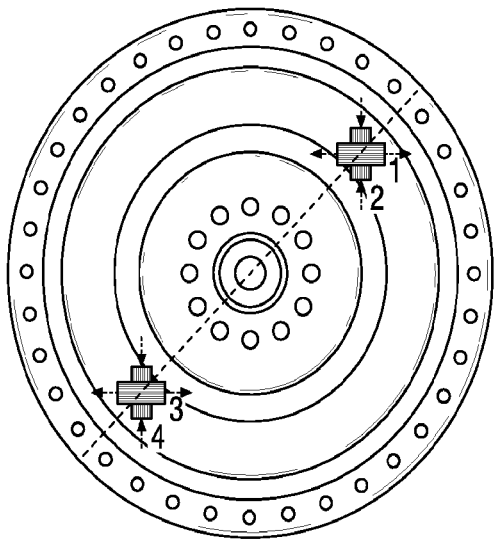
FIGS. 22A-22B respectfully show nonlimiting examples of strain gauge orientations for a Wheatstone bridge or two Wheatstone bridges.
Figure 22B:
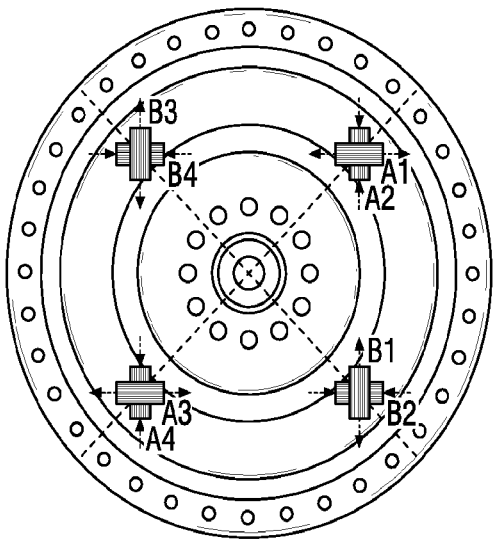

FIG. 21 shows a single node tensor. The principle components are 45 degrees offset to the ray passing through the point. FIG. 22 shows a Wheatstone Bridge where resistors indicate the variable resistance strain gauges. In some embodiments, a full balanced Wheatstone bridge is used to cancel out strain due to temperature variation and off-axis loading. The orientation of the gauges is such that the neighboring arms of the Wheatstone bridge align with opposite tensors of the principle strain. Namely, while gauges one ($R_1$) and three ($R_3$) are being extended, gauges two ($R_2$) and four ($R_4$) are being compressed and visa-versa. Due to the architecture of the Wheatstone bridge, this means that the signal is actually additive—the absolute value of the signal due to the compression of gauges 2 and 4 is added to the absolute value of the signal due to the extension of gauges 1 and 3. In some embodiments, the strain gauges in a Wheatstone bridge may be arranged on the output plate to measure joint torque. As noted above, the orientation of the principle strains of the face of the output plate with an applied torque are 45 degrees to a ray that passes through the center of rotation. As such, as shown in FIG. 23A, the strain gauge orientation for Wheatstone bridge may be arranged so that gauges 1 and 3 measure a horizontal component at opposing set distances away from the center, and gauges 2 and 4 measure a vertical component at opposing set distances away from the center.

One extra consideration with measuring torque on a component that is fixed to the HD flex spline 256 is that transmission of torque is irregular and the deflection of the flex spline is irregular based on the oblong shape of wave generator 254. This would produce waves in the strain data relative to the rotation of the wave generator 254 with a period of half the rotation of the wave generator. To counter this noise, two Wheatstone bridges can be used, as shown in FIG. 23B, where strain gauge orientation for two Wheatstone bridges are positioned to be orthogonal or out of phase by 180 degrees in the strain noise period. By averaging the two measures of the bridges, the torque ripple is eliminated or ripple free.

Joint Electronics Integration

Figure 23:
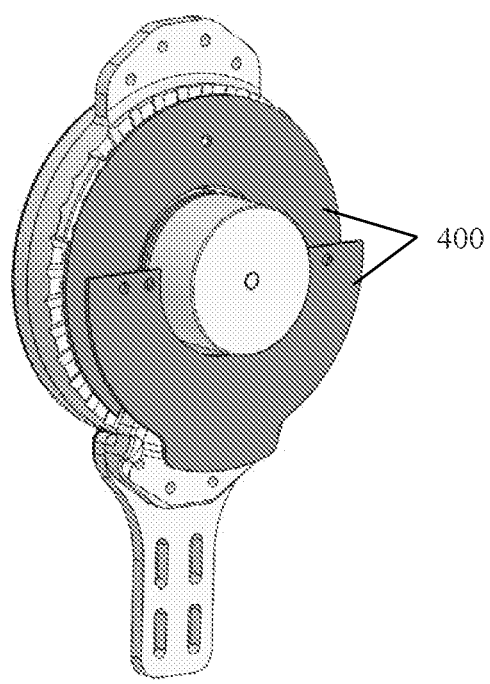
FIG. 23 shows an exemplary illustration of a joint actuator with integrated controller electronics.

In order for the actuator or joint 200 of the exoskeleton to be modular, joint control hardware may be integrated into the modular joint. FIG. 23 an integrated PCBs 400 for joint control and motor driving integrated with the actuator 200. Because of this, no electronics need to be mounted to the intermediate brace/frame components, simplifying the overall design.

Hip Brace

Figure 24:
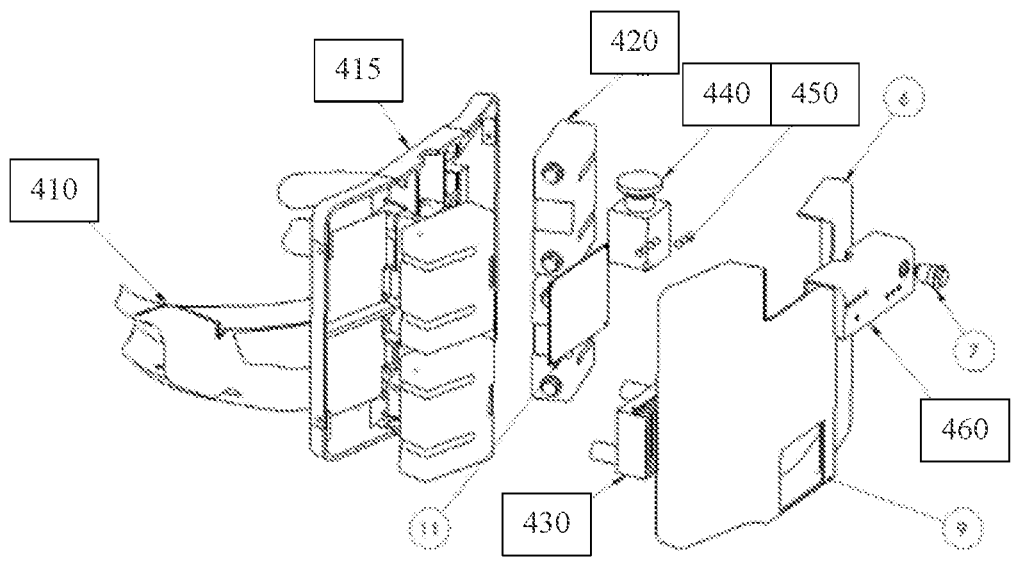
FIG. 24 shows an exemplary illustration of a hip brace assembly.

FIG. 24 shows a nonlimiting example of a hip brace assembly. The hip brace 410 may be similar to the leg braces, using the same style of reinforced carbon fiber frame molded to the user for the primary frame component. More particularly, the hip brace may provide a frame comprising a vertical support beam, a top horizontal support rib, and a bottom horizontal support rib, as well as an inner layer and an outer layer, wherein the frame is sandwiched between the inner and outer layers, and a shape of the inner and outer layers provides a level of structural rigidity desired. The hip brace further provides at least one exoskeleton attachment for coupling the brace to a joint actuator and securing attachments, wherein the securing attachments facilitate the user being secured in the brace. The brace 410 may be lined with foam for comfort. The frame also provides the attachment point for the hip actuators and the attachment for the main unit. The main unit may be attached to brace 410 with an adapter 415. The main unit may have room for the power source 420, such as one to four 12 volt batteries. In a nonlimiting example, four 3.2 Ah lithium iron phosphate batteries are utilized. These batteries 420 are balanced by the battery management circuit that constantly monitors over voltage, under voltage, current draw, as well as controlling for improper polarity. A balanced 12V line goes to a boost converter or voltage multiplier 430. For example, boost converter 430 may boosts the voltage to a regulated 48V, i.e. the voltage used by the brushless DC motors. The e-stop 440 cuts a relay to all powerlines in the exoskeleton. LED indicators 450 are used as visual cues to immediately visualize the voltage in each battery, the status of the power rails (e.g. 48V and 5V), as well as the current mode of the exoskeleton (e.g. moving, paused, etc.). These are mounted in a control panel 460 on the back.

Power Management

Figure 25:
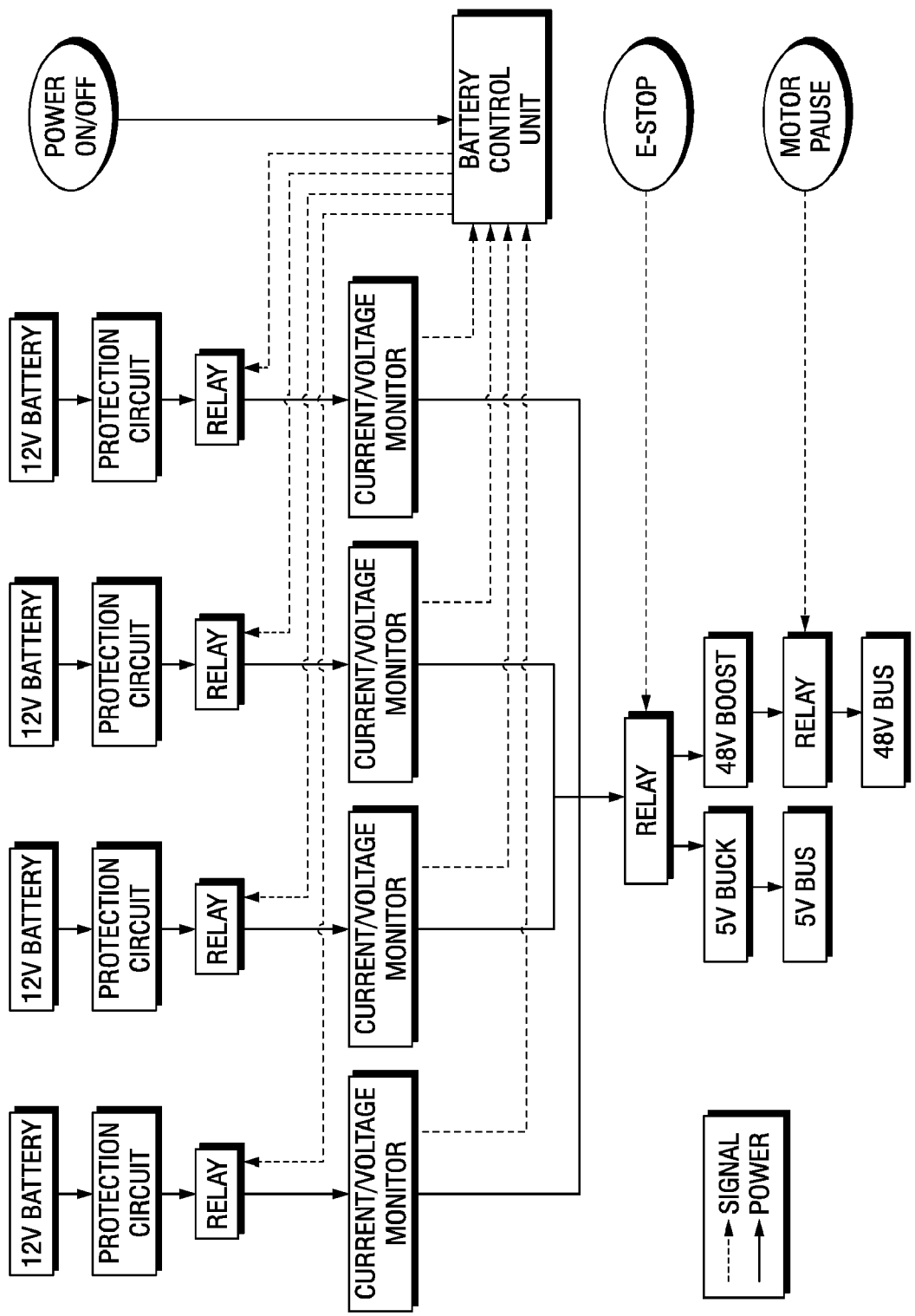
FIG. 25 shows a power management diagram.

FIG. 25 shows a nonlimiting example power management diagram. The power supply for the exoskeleton comprises a 48 volt bus and a 5 volt bus. The 48V line is for powering the motors and the 5V line is for all other electronic components. The power source may comprise four 12 volt lithium iron phosphate batteries in some embodiments. These may have an undervoltage and polarity protection circuit. This goes through a relay that is controlled by the battery management controller. This controller balances the battery consumption across the four batteries.

After the 12 volt lines are combined, they are passed through another relay that can be shut down by an e-stop. It is then passed to a 5V buck converter and a 48V boost converter. The boost converter output passes through another relay which is controlled by a pause button. This button effectively kills power to the motors without affecting data recording.

Foot Design

Figure 26:
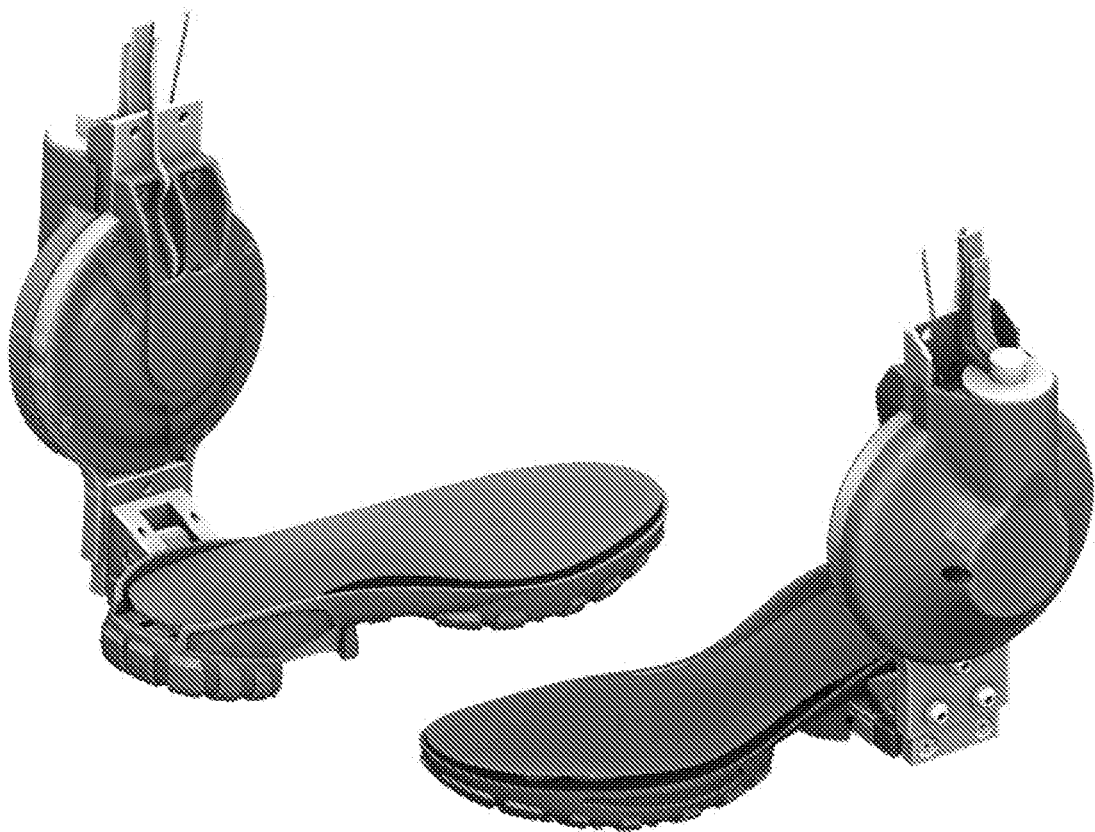
FIG. 26 shows medial (left) and lateral (right) view of the foot and ankle assembly.

FIGS. 26A-26B shows medial (left) and lateral (right) view of the foot and ankle assembly. The overall foot design has a few key features. These include:

Transferring sagittal plane torques to the users' limb between their lower leg and their foot via the ankle actuator.

Allow for some damped passive inversion and eversion of the ankle.

Detect heel and toe contact with the ground.

Detect the amount of flexing in the shank of the foot.

Provide traction.

Allow for turning on a variety of surfaces.

Withstand normal use loading for an extended period of time.

Figure 27A:
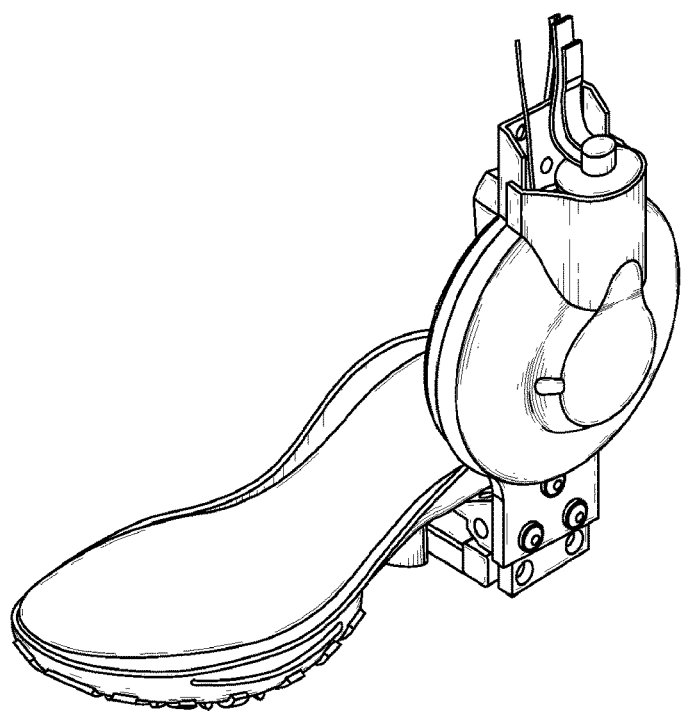
FIGS. 27A-27B respectively show the primary components of the foot assembly and an exploded view of the foot assembly.
Figure 27B:
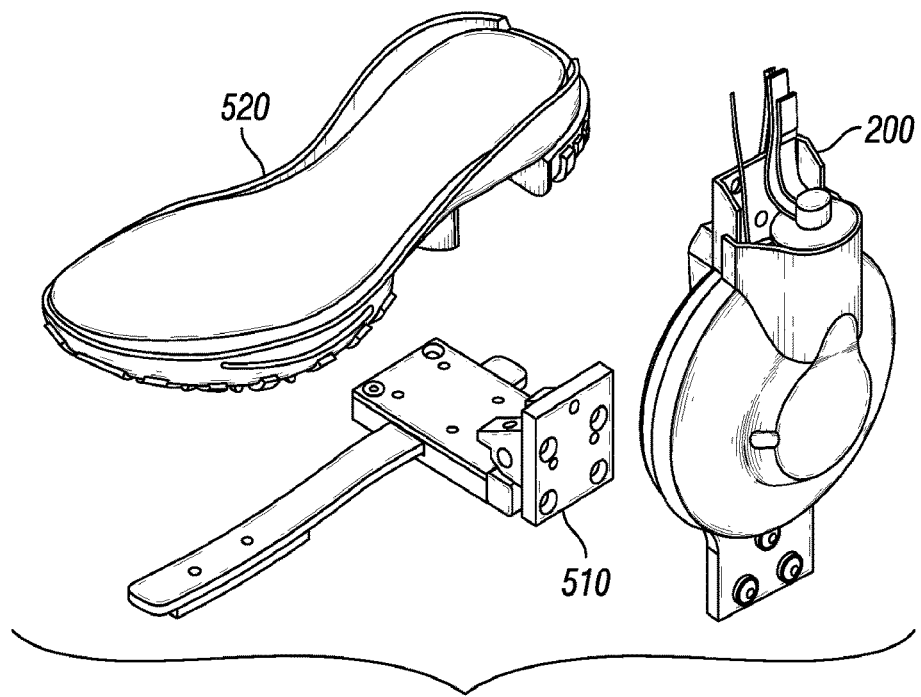

The foot assembly comprises three main components— the actuator, the attachment mechanism and the instrumented shoe. FIGS. 27A-27B respectively show the primary components of the foot assembly and an exploded view of the foot assembly including the actuator 200, the attachment mechanism 510 and the instrumented shoe 520. Only the bottom or sole of the shoe is shown for clarity.

The actuator is described in detail above. The attachment mechanism 510 is used to attach the actuator to the shoe and also acts as the passive inversion and eversion joint, as well as the main stiffness regulator in the metatarsophalangeal joint (MTP joint). The attachment may comprise an attachment bracket for attachment to the actuator 200, and a base that secures the modified shoe 520. The flexing of the MTP joint is also measured across the shank by a flex sensitive resistor. The upper portion of the foot is a modified shoe 520 that includes force sensitive resistors for detecting foot contact and the connections to the attachment mechanism. The remaining shoe structure is used as a comfortable, ergonomic attachment between the exoskeleton and the user's foot.

FIG. 28 shows an instrumented shoe assembly, which comprises the shoe 520 with a modified sole 530, two force sensor (e.g. force sensitive resistor (FSR)) modules 540, and an upper and lower sensor module plate 550, 560. The sensors 540 and the mounting plates 570 are all under the user's insole 580. As shown, the sensor 540, module plates 550,560, and mounting plate 570 are position where the heel and ball of the foot of the user will be placed. As a nonlimiting example, the instrumented shoe comprised a modified running shoe that is sized to fit the user and the force sensitive resistor (FSR) modules. The heel of the shoe 520 is carved to allow for the attachment plate 510 of the exoskeleton ankle with 3D printed screw backing plates to match the contour of the shoe and fit underneath the user's insole. The FSR modules 540 are placed such that sensors detect both heel strike and toe-off, important markers in segmenting the gait cycle. The rigid FSR module plates 550, 560 may have small raised dimples that focus the load directly on the FSRs' force sensitive region to maximize the usefulness of the sensor. Additionally, two sensors are used for both the toe and the heel to have some redundancy in case of sensor failure.

The attachment mechanism 510 primarily comprises the plate to attach the shoe to the actuator and the shank component. The shank component would ordinarily be composed of a composite laminate that would allow for a spring like action across the MTP joint. This spring like shank would be replaceable. Different shank geometries and materials lead to different spring factors which could be used to tune the assembly to a user's specific need.

Shank Assembly Design

FIG. 29 shows a shank assembly of the exoskeleton, which includes the brace and the connections to the knee and ankle actuators. This assembly transmits the torque from the exoskeleton to the user's lower leg. The shank is the assembly that connects the ankle joint to the knee joint. A variety of mechanical systems can be used to attach the two joints due to the modular attachment points including an adjustable length system, a rigid metal fixed length system, or in this nonlimiting example, a composite connection that serves both as the attachment brace for the user and the structural support between the joints. In some embodiments, the shank is also where the control electronics for the ankle joint may be located.

FIGS. 30A-30B show and assembled and exploded view of components of the shank assembly 600 including the generic straps 610, the brace 620, the knee-to-shank adapter 630 (optional), the housing 640 (optional), the joint control electronics 650 (optional, e.g. hip/knee), and the ankle-to-shank adapter 660 (optional). In some embodiments, straps 610 may be utilized to secure the user's limb into the brace 620. In other embodiments, another brace may be provided that attaches to brace 620 (e.g. FIG. 9B). In some embodiments, any suitable closure system may be utilize for the brace(s), such as a Boa® Closure System, which utilizes a winding knob, a cable, and connection points. The cable tightens when the knob is turned, drawing together the separate components of the brace. This allows for adjustable brace tightness as well as easy disconnect. In some embodiment, the tubes for such a Boa closure system may be created during the 3D printing of the brace(s).

The brace itself 620 may include various features of the brace design discussed previously above. The brace 620 shown can either be directly attached to the joints 200 or include an adapter plate 630, 660 with some slight adjustability. The adapter plates 630, 660 may also aid in securing control electronics 650 and/or housing 640. The adapter plate(s) 630, 660 may also allow for a wider variety of attachment methods to the braces with a common joint architecture. As noted previously, some embodiments may incorporate joint control electronics into the actuator. However, other embodiments may incorporate joint control electronics 650 into the brace assembly instead. The housing 640 protects any cables or other sensitive parts of the exoskeleton system, such as the cables running from the knee control board to the ankle control board and to protect the ankle control electronics mounted to the outside of the brace.

In some embodiments, the shank brace may be located on the posterior surface of the lower leg. It is manufactured for a custom fit to the individual based on a 3D scan of the user's limb. The brace may comprise a frame sandwiched between inner/outer shells. As a nonlimiting example, this is done using a carbon fiber layup over a lightweight plastic frame. The frame creates a stiffer structure than the carbon fiber layup would be able to do alone. This allows for higher strength to carry the load of the exoskeleton as well as the forces applied on or by the user's leg. As a nonlimiting example, the brace may be the customizable orthodic/prosthetic discussed previously above. As a nonlimiting example, the brace may be made up of an inner lightweight plastic frame sandwiched between a carbon fiber composite. The interior surface is padded with foam for the user's comfort.

Thigh Assembly Design

Figure 31:
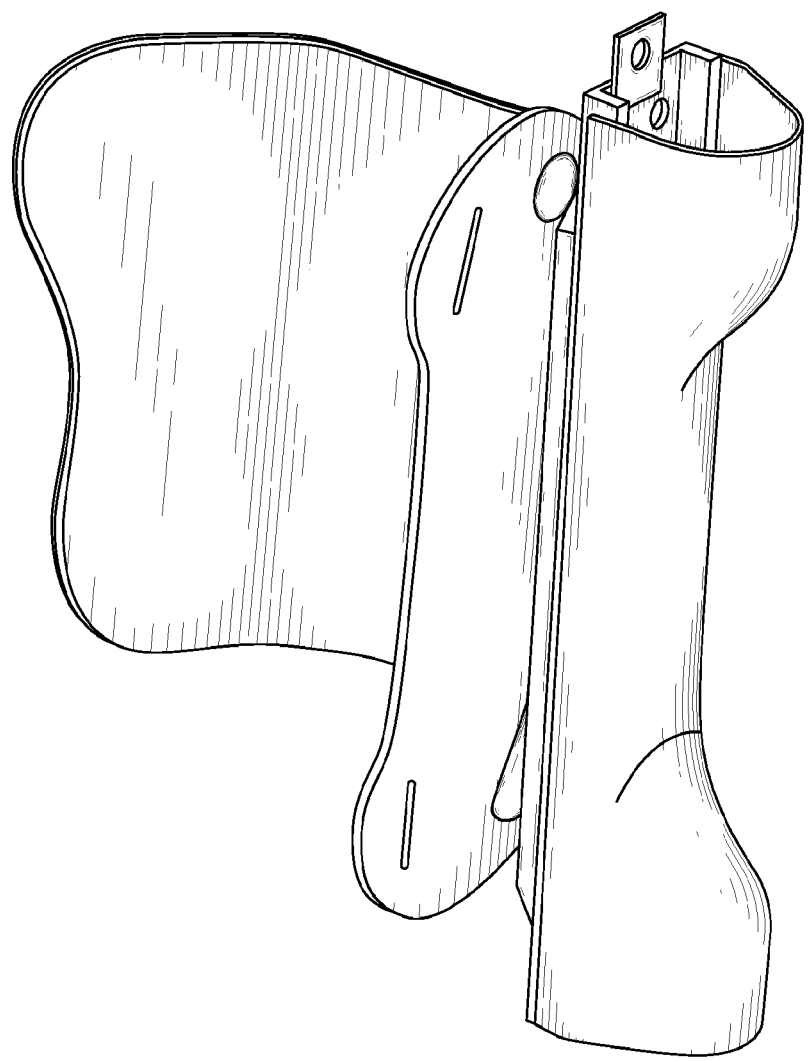
FIG. 31 shows a thigh assembly.

FIG. 31 shows a thigh assembly. In the interest of brevity, it is noted that the above noted features discussed for the shank assembly design also apply to the thigh assembly design, but are not repeated in detail below. Like the shank assembly design discussed above, the thigh assembly may provide a brace, generic straps or another brace, an optional first joint adapter (e.g. thigh-to-knee), optional housing, optional joint control electronics (e.g. knee/ankle), and optional second joint adapter (hip-to-thigh). The thigh assembly allows for the transmission of torque between the exoskeleton and the user's upper leg. The thigh design is very similar to the shank assembly design discussed above, where similar components serve the same purpose. In some embodiments, the motor sides for both the hip and the knee joint are oriented towards the thigh brace segment (i.e. the thigh joint actuator has the motor shaft pointing up and the knee joint actuator has the motor shaft facing down). In embodiments where the joint control electronics are provided by the brace assemblies, the thigh housing may include the control electronics for both the hip and the knee actuators.

Hip Assembly Design

Referring back to FIGS. 9A-9D, the hip assembly is generally similar to the thigh and shank assemblies, but does not require joint attachments at both ends of the hip brace. The one or more hip brace(s) may comprise braces conforming to the prior brace designs discussed above. Like the shank assembly design discussed above, the hip assembly may provide brace(s), generic straps or another brace, an optional joint adapter (e.g. hip-to-thigh), and an optional housing (or main unit). In addition, as discussed previously regarding FIG. 25, the hip assembly may also provide a primary battery, overall system controller, user interface connections, emergency stops, and other electronics for the exoskeleton system.

Crutch Design

The crutches serve three primary purposes including (1) supporting the user of the exoskeleton to allow them to dynamically balance; (2) user interface controls easily accessible for changing modes, powering the system on and off, and emergency stopping; and (3) measuring the user interaction forces on the crutches to determine how the individual is using the crutch and exoskeleton combination. The first point is primarily important and so standard forearm crutches are preferred with large, conforming non-slip feet at the end of the crutch. User interface controls are easily reconfigurable depending on the user's capability, environment, clinician interaction and tasks that need to be performed.

Measuring the user's interaction forces is an important metric for how the user is utilizing the exoskeleton. This can be measured by determining how much weight they are putting on either crutch relative to the location in the gait cycle. Such information is critical for clinicians to diagnose the use or misuse of the system and assist in training the users as well as document quantitative changes in the reliance arm strength versus exoskeleton support. This is done with strain gauges mounted on the shaft of the crutch. The strain gauges measure the compression of the crutch tube which can be translated into loading force. The loading force can be compared to the user's weight and the point in the gait cycle to assess their use of the system.

Embodiments described herein are included to demonstrate particular aspects of the present disclosure. It should be appreciated by those of skill in the art that the embodiments described herein merely represent exemplary embodiments of the disclosure. Those of ordinary skill in the art should, in light of the present disclosure, appreciate that many changes can be made in the specific embodiments described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

What is claimed is:

1. A lower limb exoskeleton comprising: a power control unit comprising a power supply;
   a plurality of joint actuators that are modular, wherein each of the plurality of joint actuators comprises an electric motor, an input arm, and an output arm, wherein each of the plurality of joint actuators provides rotary motion between the input arm and the output arm;
   a hip assembly, wherein the hip assembly comprises a hip brace;
   a hip actuator, wherein the hip actuator is one of the plurality of joint actuators, and the input arm of the hip actuator is coupled to the hip assembly;
   at least one thigh assembly, wherein the thigh assembly comprises a thigh brace and a top end of the thigh brace is coupled to the output arm of the hip actuator, the thigh brace bearing the load between the hip actuator and a knee actuator, and the thigh assembly provides a thigh housing;
   wherein the knee actuator is one of the plurality of joint actuators, and the input arm of the knee actuator is coupled to a bottom end of the thigh assembly;

at least one shank assembly, wherein the shank assembly comprises a shank brace and a top end of the shank brace is coupled to the output arm of the knee actuator, the shank brace bearing the load between the knee actuator and an ankle actuator, and the shank assembly provides a shank housing;

wherein the ankle actuator is one of the plurality of joint actuators, and the input arm of the ankle actuator is coupled to a bottom end of the shank assembly;

at least one foot assembly, wherein the foot assembly comprises a foot attachment coupled to the output arm of the ankle actuator and a shoe;

wherein each of the hip brace, the thigh brace, and the shank brace are open form braces that only cover a posterior portion of a user's limb, and that are personalized to the user's limb geometry wherein each of the hip brace, the thigh brace, and the shank brace further comprise:

a frame comprising a vertical support beam, a top horizontal support rib, and a bottom horizontal support rib;

an inner layer and an outer layer, wherein the frame is sandwiched between the inner and outer layers, and the brace formed is rigid, and unmalleable;

at least one pressure sensor embedded in the brace to provide detection of brace pressure;

and at least one exoskeleton attachment for coupling the brace to one of the plurality of joint actuators.

2. The exoskeleton of claim 1, wherein each of the plurality of joint actuators comprises:

the electric motor, wherein a motor shaft is arranged parallel to a vertical axis;

a right angle gear assembly coupled to the electric motor, wherein the right angle gear assembly translates rotation of the motor into rotation of an output shaft of the right angle gear assembly about a joint axis of rotation;

wherein the input arm is secured to the right angle gear assembly, and the input arm provides a first attachment arm, and the output shaft of the right angle gear assembly passes through an opening through a body of the input arm;

wherein the output arm provides a second attachment arm;

and a strain wave gear assembly coupling the input arm to the output arm, wherein the output shaft of the electric motor feeds a center of the strain wave gear assembly, and the strain wave gear assembly is sandwiched between the input arm and the output arm.

3. The exoskeleton of claim 2, wherein the strain wave gear assembly comprises a wave generator, strain wave spline, and ring spline.

4. The exoskeleton of claim 3, wherein the electric motor, the right angle gear, the input arm, and the ring spline form a first group of linked components; the output shaft and the wave generator form a second group of linked components; and the strain wave spline and the output arm form a third group of linked components.

5. The exoskeleton of claim 2, wherein each of the plurality of joint actuators further comprises a cross roller bearing connecting the input arm to the output arm.

6. The exoskeleton of claim 2, wherein each of the plurality of joint actuators further comprises at least one hard stop that controls the range of motion of one of the plurality of actuators.

7. The exoskeleton of claim 6, wherein each of the plurality of joint actuators further comprises a trigger pin to power off the motor when the input arm contacts the trigger pin.

8. The exoskeleton of claim 2, wherein each of the plurality of joint actuators further comprises a rotary encoder or a shaft encoder.

9. The exoskeleton of claim 2, wherein each of the plurality of joint actuators further comprises an inertial measurement unit, wherein the inertial measurement unit provides acceleration, angular velocity, and position measurements for three axes.

10. The exoskeleton of claim 2, wherein each of the plurality of joint actuators further comprises an output plate transmitting all output torque received from the strain wave gear assembly to the output arm.

11. The exoskeleton of claim 10, wherein a plurality of strain gauges of a Wheatstone bridge are arranged on the output plate to measure joint torque.

12. The exoskeleton of claim 1, wherein each of the hip brace, the thigh brace, and the shank brace further comprise straps, wherein the straps facilitate the user's limb being secured in the brace.

13. The exoskeleton of claim 1, wherein the at least one exoskeleton attachment of both the thigh brace and the shank brace comprise a top exoskeleton attachment and a bottom exoskeleton attachment, wherein the vertical support beam runs between the top and bottom exoskeleton attachments.

14. The exoskeleton of claim 13, wherein the exoskeleton further comprises joint adapters for securing the plurality of joint actuators to the hip brace, thigh brace, or shank brace.

15. The exoskeleton of claim 1, wherein the foot attachment provides a base securing the shoe.

16. The exoskeleton of claim 15, wherein the shoe comprises a sole and an insole, and the shoe further provides a heel sensor assembly and a toe sensor assembly sandwiched between the sole and the insole, and wherein each of the heel assembly and the toe sensor assembly comprise a force sensitive resistor (FSR) module sandwiched between an upper module plate and a lower module plate.

17. The exoskeleton of claim 1, further comprising a pair of crutches, wherein a plurality of strain gauges are mounted on the shaft of the pair of crutches.

18. The exoskeleton of claim 1, wherein each of the hip brace, the thigh brace, and the shank brace are 3D printed.

19. The exoskeleton of claim 1, wherein the user is a child.

* * * * *